(12) United States Patent
Luo

(10) Patent No.: US 11,942,190 B2
(45) Date of Patent: *Mar. 26, 2024

(54) METHOD AND SYSTEM FOR EVALUATING REACTIVITY IN SOURCE ROCK EVALUATION

(71) Applicant: SAUDI ARABIAN OIL COMPANY, Dhahran (SA)

(72) Inventor: Pan Luo, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 393 days.

This patent is subject to a terminal disclaimer.

(21) Appl. No.: 17/167,584

(22) Filed: Feb. 4, 2021

(65) Prior Publication Data

US 2022/0246247 A1 Aug. 4, 2022

(51) Int. Cl.
*G16C 20/10* (2019.01)
*G01N 33/24* (2006.01)

(52) U.S. Cl.
CPC ............ *G16C 20/10* (2019.02); *G01N 33/24* (2013.01); *G01N 33/241* (2013.01)

(58) Field of Classification Search
CPC ....... G16C 20/10; G01N 33/24; G01N 33/241
See application file for complete search history.

(56) References Cited

U.S. PATENT DOCUMENTS

| | | | |
|---|---|---|---|
| 2017/0286802 A1* | 10/2017 | Mezghani | G06F 18/2413 |
| 2018/0217112 A1 | 8/2018 | Mathur | |
| 2018/0347354 A1 | 12/2018 | Li et al. | |
| 2019/0196054 A1* | 6/2019 | Csutak | E21B 49/02 |
| 2019/0369078 A1* | 12/2019 | Ducros | G01N 33/241 |
| 2020/0408090 A1* | 12/2020 | Kadayam Viswanathan | E21B 49/02 |
| 2022/0127959 A1* | 4/2022 | Khalifa | G01V 99/005 |

FOREIGN PATENT DOCUMENTS

WO   2018/170035 A1   9/2018

OTHER PUBLICATIONS

Zhongtian Mao "Apparent Activation Energies in Complex Reaction Mechanisms: A simple Relationship via Degrees of Rate Control", pp. 9465-9473 (Year: 2019).*

(Continued)

*Primary Examiner* — Michael J Dalbo
*Assistant Examiner* — Kaleria Knox
(74) *Attorney, Agent, or Firm* — Osha Bergman Watanabe & Burton LLP

(57) ABSTRACT

A method for evaluating thermal reactivity in source rock evaluation may include obtaining information relating to various source rock samples. The method may include determining reactivities of source rocks corresponding to the various source rock samples. The source rocks may be at a same level of thermal maturity in an area of interest. The method may include interpreting kinetic parameters derived from the plurality of source rock samples. The method includes comparing published, archived and measured kinetic parameters of source rocks in the area of interest. The method may include converting complex format of kinetic parameters into a single variable for reactivity for evaluation and characterization of source rock in the area of interest.

20 Claims, 22 Drawing Sheets

(56) References Cited

OTHER PUBLICATIONS

David Wood "Re-Establishing the Merits of Thermal maturity and Petroleum Generation Multi-Dimensional Modeling with an Arrhenius Equation Using a Single Activation Energy" Jornal of Earth Science, vol. 28, No. 5, pp. 804-834 (Year: 2017).*

Nordeng "Evaluating Source Rock maturity Using Muti-Smple Kinetic Parameters from the Bakken Formation (Miss.-Dev.), Williston Basin, ND" , pp. 1-19 (Year: 2013).*

Ducros, Mathieu, "Source Rock Kinetics: Goal and Perspectives", Search and Discovery Article #41822, Datapages, Jul. 2016 (30 pages).

Chen, Zhucheng et al., "Quick Evaluation of Source Rock Kerogen Kinetics Using Hydrocarbon Pyrograms from Regular Rock-Eval Analysis", Engery & Fuels, ACS Publications, American Chemical Society, vol. 31, 2017, pp. 1832-1841 (10 pages).

Kamga, Albert Willy Nguena, "Low-Temperature Artificial Maturation Studies of Type II and Type III Kerogens: Implications for Biogenic Gas Production", Chemistry & Biochemistry Theses & Dissertations, Old Dominion University ODU Digital Commons, May 2016 (249 pages).

Bin, Zhang et al., "Kinetic simulation of hydrocarbon generation and its application to in-situ conversion of shale oil", Petroleum Exploration and Development, ScienceDirect, Elsevier B.V., vol. 46, Issue 6, Dec. 2019, pp. 1288-1296 (9 pages).

Chen, Zhucheng et al., "Inversion of source rock hydrocarbon generation kinetics from Rock-Eval data", Fuel, ScienceDirect, Elsevier B.V., vol. 194, 2017, pp. 91-101 (11 pages).

Cornford, Chris et al., "Geochemical truths in large data sets. I: Geochemical screening data", Organic Geochemistry, Elsevier Science Ltd., vol. 29, No. 1-3, 1998, pp. 519-530 (12 pages).

Dieckmann, V. and M. Keym, "A new approach to bridge the effect of organofacies variations on kinetic modelling and geological extrapolations", Organic Chemistry, Elsevier Ltd., vol. 37, Apr. 2006, pp. 728-739 (12 pages).

Hackley, Paul C. and Brian J. Cardott, "Application of organic petrography in North American shale petroleum systems: A review", International Journal of Coal Geology, ScienceDirect, Elsevier B.V., vol. 163, Jun. 2016, pp. 8-51 (44 bages).

Hantschel, T. and A.I. Kauerauf, "Petroleum Generation", Fundamentals of Basin and Petroleum Systems Modeling, Springer-Verlag Berlin Heidelberg, 2009, pp. 151-198 (48 pages).

Jarvie, Daniel M., "Factors affecting Rock-Eval derived kinetic parameters", Chemical Geology, Elsevier Science Publishers B.V., vol. 93, 1991, pp. 79-99 (21 pages).

Keym, Matthias et al., "Source rock heterogeneity of the Upper Jurassic Draupne Formation, North Viking Graben, and its relevance to petroleum generation studies", Organic Geochemistry, ScienceDirect, Elsevier Ltd., vol. 37, 2006, pp. 220-243 (24 pages).

"Kinetics2000TM", User Manual, Humble Instruments & Services, Inc., pp. 1-48 (48 pages).

Pepper, Andrew S. and Peter J. Corvit, "Simple kinetic models of petroleum formation. Part I: oil and gas generation from kerogen", Marine and Petroleum Geology, Elsevier Science Ltd., vol. 12, No. 3, 1995, pp. 291-319 (29 pages).

Peters, Kenneth E. et al., "Evaluation of kinetic uncertainty in numerical models of petroleum generation", AAPG Bulletin, the American Association of Petroleum Geologists, vol. 90, No. 3, Mar. 2006, pp. 387-403 (17 pages).

Peters, Kenneth E. et al., "Petroleum generation kinetics: Single versus multiple heating-ramp open-system pyrolysis", AAPG Bulletin, the American Association of Petroleum Geologists, vol. 99, No. 4, Apr. 2015, pp. 591-616 (26 pages).

Peters, K.E. et al., "Guidelines for kinetic input to petroleum system models from open-system pyrolysis", Marine and Petroleum Geology, ScienceDirect, Elsevier Ltd., vol. 92, 2018, pp. 979-986 (8 pages).

Peters, Kenneth E. and Mary Rose Cassa, "Applied Source Rock Geochemistry", The Petroleum System—from source to trap, AAPG Memoir 60, 1994, pp. 93-120 (28 pages).

Schaefer, R.G. et al., "Determination of gross kinetic parameters for petroleum formation from Jurassic source rocks of different maturity levels by means of laboratory experiments", Organic Geochemistry, Pergam Press plc, vol. 16, No. 1-3, 1990, pp. 115-120 (6 pages).

Schenk, H.J. et al., "Kinetics of Petroleum Formation and Cracking", Petroleum and Basin Evolution, Springer-Verlag Berlin, 1997, pp. 231-269 (39 pages).

Schenk, H.J. and B. Horsfield, "Using natural maturation series to evaluate the utility of parallel reaction kinetics models: an investigation of Toarcian shales and Carboniferous coals, Germany", Organ Geochmistry, Elsevier Science Ltd., vol. 29, No. 1-3, 1998, pp. 137-154 (18 pages).

Tegelaar, Erik and Rohinton A. Noble, "Kinetics of hydrocarbon generation as a function of the molecular structure of kerogen as revealed by pyrolysis-gas chromatography", Organic Geochemistry, Elsevier Science Ltd., vol. 22, No. 3-5, 1994, pp. 543-574 (32).

International Search Report and Written Opinion of the International Searching Authority issued in corresponding International Application No. PCT/US2022/015269, dated May 2, 2022 (15 pages).

International Search Report and Written Opinion of the International Searching Authority issued in corresponding International Application No. PCT/US2022/015286, dated May 19, 2022 (22 pages).

Sykes, R. and L.R. Snowdon, "Guidelines for assessing the petroleum potential of coaly source rocks using Rock-Eval pyrolysis", Organic Geochemistry, ScienceDirect, Pergamon, vol. 33, 2002, pp. 1441-1455 (15 pages).

Behar, F., et al., "Comparison of artificial maturation of lignite in hydrous and nonhydrous conditions", Organic Geochemistry, ScienceDirect, Pergamon, vol. 34, 2003, pp. 575-600 (26 pages).

Wood, David A., "Re-Establishing the Merits of Thermal Maturity and Petroleum Generation Multi-Dimensional Modeling with an Arrhenius Equation Using a Single Activation Energy"; Journal of Earth Science; vol. 28, Issue 5; pp. 804-834; Oct. 13, 2017 (31 pages).

Mao, Zhongtian et al., "Apparent Activation Energies in Complex Reaction Mechanisms: A Simple Relationship via Degrees of Rate Control"; ACS Catalysis 2019; vol. 9, Issue 10; pp. 9465-9473; Aug. 27, 2019 (9 pages).

* cited by examiner

| Well | Depth[1] | Seq.#[2] | S1 | S2 | Tmax | S3 | TOC | HI | OI | VRE.t[3] | GRo[4] | VRE.g[5] | A[6] | WA-Ea[7] |
|---|---|---|---|---|---|---|---|---|---|---|---|---|---|---|
| | ft | | mg HC/g Rock | mg HC/g Rock | °C | mg CO2/g Rock | % | mg HC/g Rock | mg CO2/g Rock | % | % | % | s⁻¹ | kcal/mol |
| Well T | t237 | | 1.09 | 57.82 | 416.5 | 0.74 | 11.34 | 510 | 6.5 | 0.47 | 0.68 | 0.54 | 9.77E+14 | 56.23 |
| Well S | s281 | (1) | 0.27 | 5.12 | 427.9 | 0.26 | 2.34 | 219 | 11.1 | 0.68 | | | 5.58E+13 | 52.87 |
| Well S | s379 | (2) | 3.22 | 54.56 | 420.5 | 0.46 | 10.71 | 509 | 4.3 | 0.54 | | | 2.99E+14 | 54.89 |
| Well S | s444 | (3) | 1.5 | 18.21 | 419.5 | 0.33 | 5.37 | 339 | 6.1 | 0.53 | | | 4.21E+14 | 55.35 |
| Well S | s480 | (4) | 3.21 | 38.71 | 418.3 | 0.26 | 8.56 | 452 | 3.0 | 0.50 | | | 1.26E+16 | 60.01 |
| Well S | s382 | | 2.14 | 33.4 | 418.0 | 0.05 | 7.53 | 444 | 0.7 | 0.50 | 0.76 | 0.61 | | |
| Well S | s491 | (5) | 1.46 | 20.99 | 418.9 | 0.33 | 6.2 | 338 | 5.2 | 0.51 | | | 3.18E+15 | 57.97 |
| | Average | | | | 420.5 | | | | | 0.55 | | | | |
| | Stdev | | | | 3.7 | | | | | 0.07 | | | | |
| Well M | m3423 | (1) | 2.03 | 18.4 | 445.0 | 0.35 | 5.9 | 312 | 5.9 | 1.00 | | | 9.2E+14 | 57.74 |
| Well M | m3431 | (2) | 0.41 | 1.91 | 446.0 | 0.3 | 0.9 | 212 | 33.3 | 1.02 | | | 6.78E+15 | 60.72 |
| Well M | m3581 | (3) | 2.93 | 13.6 | 440.0 | 0.23 | 6.52 | 209 | 3.5 | 0.91 | 1.07 | 0.86 | | |
| Well M | m3587 | (4) | 2.65 | 11.99 | 440.0 | 0.26 | 5.93 | 202 | 4.4 | 0.91 | | | 3.98E+14 | 56.05 |
| Well M | m3603 | (4) | 2.34 | 9.65 | 439.8 | 0.32 | 6.19 | 156 | 5.2 | 0.91 | | | 2.68E+15 | 58.54 |
| Well M | m3611 | (5) | 2.56 | 7.8 | 440.2 | 0.25 | 5.16 | 151 | 4.8 | 0.91 | | | 2.33E+15 | 58.48 |
| Well M | m3616 | (6) | 2.71 | 11.09 | 438.7 | 0.28 | 6.16 | 180 | 4.5 | 0.88 | | | 2.59E+15 | 59.33 |
| | Average | | | | 441.4 | | | | | 0.93 | | | | |
| | Stdev | | | | 2.9 | | | | | 0.05 | | | | |
| Well A | a5139 | | 1.02 | 2.81 | 475 | 0.23 | 5.02 | 56 | 4.6 | 1.56 | 1.78 | 1.43 | n.a. | n.a. |

FIG. 9

| Sample | Well S - s6379 |  |
|---|---|---|
| A (s^-1) | 2.9911E+14 |  |
| WA Ea (kcal/mol) | 54.89 |  |
| Fraction | Ea | Fract.*Ea |
| % | cal/mol | kcal/mol |
| 0.14 | 41000 | 0.06 |
| 0 | 42000 | 0.00 |
| 0.2 | 43000 | 0.09 |
| 0.1 | 44000 | 0.04 |
| 0.17 | 45000 | 0.08 |
| 0.16 | 46000 | 0.07 |
| 0.2 | 47000 | 0.09 |
| 0.32 | 48000 | 0.15 |
| 0.48 | 49000 | 0.24 |
| 0.72 | 50000 | 0.36 |
| 0.47 | 51000 | 0.24 |
| 0.88 | 52000 | 0.46 |
| 1.6 | 53000 | 0.85 |
| 44.13 | 54000 | 23.83 |
| 17.85 | 55000 | 9.82 |
| 18.84 | 56000 | 10.55 |
| 8.37 | 57000 | 4.77 |
| 2.21 | 58000 | 1.28 |
| 1.14 | 59000 | 0.67 |
| 1.05 | 60000 | 0.63 |
| 0 | 61000 | 0.00 |
| 0.28 | 62000 | 0.17 |
| 0.69 | 63000 | 0.43 |
| 0 | 64000 | 0.00 |
| 0 | 65000 | 0.00 |
| 0 | 66000 | 0.00 |
| 0 | 67000 | 0.00 |
| 0 | 68000 | 0.00 |
| 0 | 69000 | 0.00 |
| 0 | 70000 | 0.00 |

FIG. 10A

| Sample | Well M - m3431 | |
|---|---|---|
| A (s^-1) | 6.7820E+15 | |
| WA Ea (kcal/mol) | 60.72 | |
| Fraction | Ea | Fract.*Ea |
| % | cal/mol | kcal/mol |
| 0 | 41000 | 0.00 |
| 0 | 42000 | 0.00 |
| 0 | 43000 | 0.00 |
| 0.58 | 44000 | 0.26 |
| 0.02 | 45000 | 0.01 |
| 0.6 | 46000 | 0.28 |
| 0.16 | 47000 | 0.08 |
| 0.45 | 48000 | 0.22 |
| 0.23 | 49000 | 0.11 |
| 0.28 | 50000 | 0.14 |
| 0.42 | 51000 | 0.21 |
| 0.14 | 52000 | 0.07 |
| 0.67 | 53000 | 0.36 |
| 0.18 | 54000 | 0.10 |
| 0.89 | 55000 | 0.49 |
| 0.67 | 56000 | 0.38 |
| 1.6 | 57000 | 0.91 |
| 0 | 58000 | 0.00 |
| 0 | 59000 | 0.00 |
| 44.06 | 60000 | 26.44 |
| 16.02 | 61000 | 9.77 |
| 16.74 | 62000 | 10.38 |
| 5.54 | 63000 | 3.49 |
| 3.79 | 64000 | 2.43 |
| 3.74 | 65000 | 2.43 |
| 0 | 66000 | 0.00 |
| 1.36 | 67000 | 0.91 |
| 1.11 | 68000 | 0.75 |
| 0 | 69000 | 0.00 |
| 0.75 | 70000 | 0.53 |

FIG. 10B

METHOD AND SYSTEM FOR EVALUATING REACTIVITY IN SOURCE ROCK EVALUATION

BACKGROUND

Kinetic parameters are an input in basin modeling to determine an onset and rate of hydrocarbon generation as well as a depth or a temperature of oil and gas generation windows. Kinetic parameters that describe chemical reaction rates include an activation energy and a frequency factor. To this end, most petroleum system modeling assumes that oil and gas generation can be described by a series of parallel first-order kinetics, where the rate of each reaction depends on the concentration of only one reactant. Basin models in which the generation of different subcomponents of the kerogen are individually stimulated (i.e., each subcomponent has a different set of frequency factors and distribution of activation energies).

SUMMARY

In general, in one aspect, embodiments disclosed herein relate to a method for evaluating thermal reactivity in source rock evaluation. The method includes obtaining information relating to various source rock samples. The method includes determining reactivities of source rocks corresponding to the various source rock samples. The source rocks are at a same level of thermal maturity in an area of interest. The method includes interpreting kinetic parameters derived from the plurality of source rock samples. The method includes comparing published, archived and measured kinetic parameters of source rocks in the area of interest. The method includes converting complex format of kinetic parameters into a single variable for reactivity for evaluation and characterization of source rock in the area of interest.

In general, in one aspect, embodiments disclosed herein relate to a system for evaluating thermal reactivity in source rock evaluation. The system includes a receiver that receives information relating to various resource rock samples. The system includes a processor that determines reactivities of source rocks corresponding to the various resource rock samples. The source rocks are at a same level of thermal maturity in an area of interest. The processor interprets kinetic parameters derived from the various source rock samples. The processor compares published, archived and measured kinetic parameters of source rocks in the area of interest. The processor converts complex format of kinetic parameters into a single variable for reactivity for evaluation and characterization of source rock in the area of interest.

In general, in one aspect, embodiments disclosed herein relate to a non-transitory computer readable medium storing instructions executable by a computer processor. The instructions include functionality for obtaining information relating to various resource rock samples. The instructions includes functionality for determining thermal reactivity of source rocks corresponding to various resource rock samples. The source rocks are at a same level of thermal maturity in an area of interest. The instructions includes functionality for interpreting kinetic parameters derived from the various source rock samples. The instructions includes comparing published, archived and measured kinetic parameters of source rocks in the area of interest. The instructions includes functionality for converting complex format of kinetic parameters into a single variable for reactivity for evaluation and characterization of source rock in the area of interest.

Other aspects of the disclosure will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIGS. 9-10B show charts for source rock pyrolysis and kinetics data in accordance with one or more embodiments.

DETAILED DESCRIPTION

Figure 1:
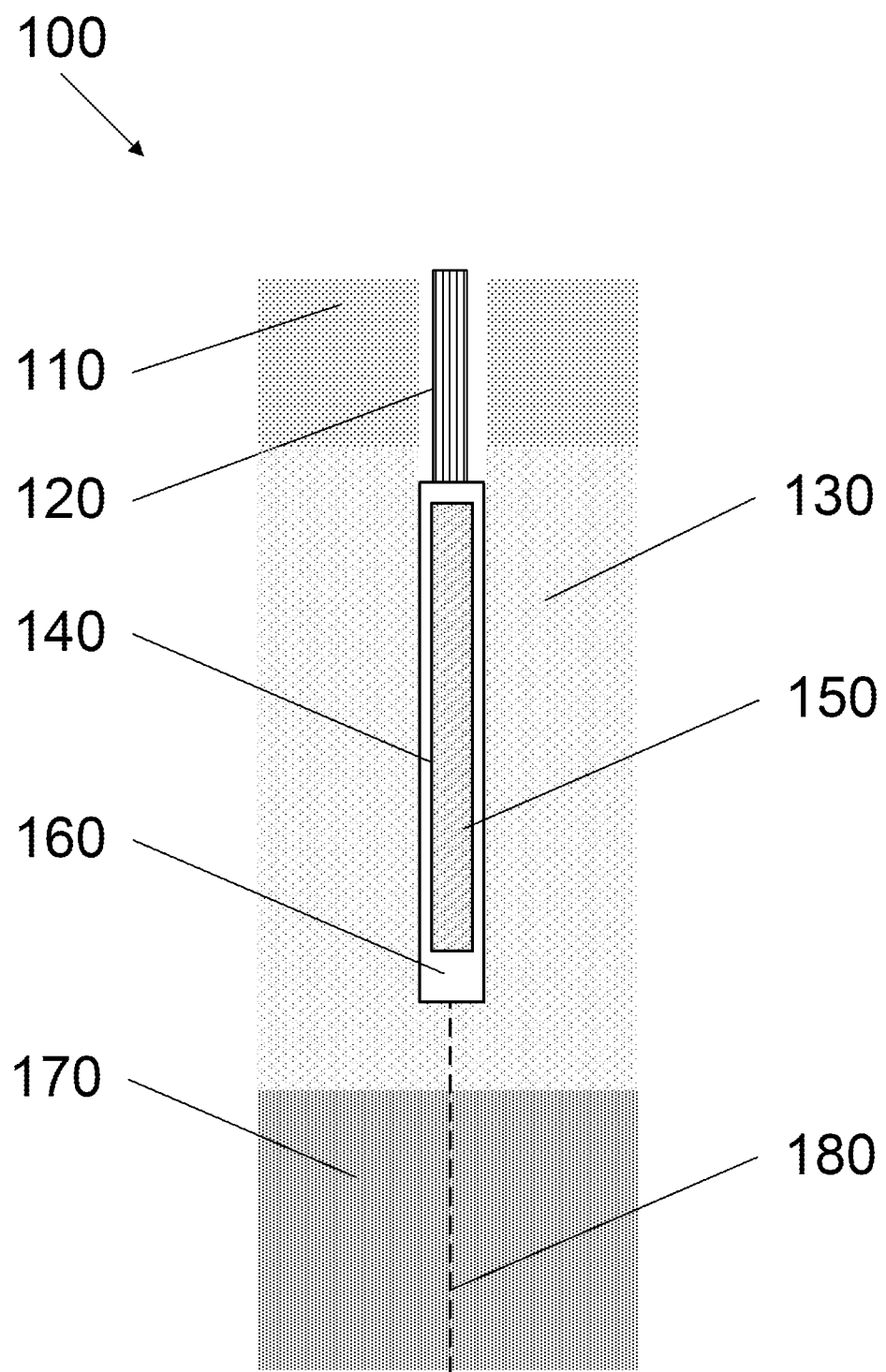
FIG. 1 shows a schematic diagram showing a cross-section view of a source rock sampling procedure in accordance with one or more embodiments.

Specific embodiments of the disclosure will now be described in detail with reference to the accompanying figures. Like elements in the various figures are denoted by like reference numerals for consistency.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In general, embodiments of the disclosure include a method and a system for evaluating reactivity in source rock evaluation. In some embodiments, the method and the system provide a simplified format of kinetic parameters and a graphic approach to evaluate reactivities of source rocks. In some embodiments, the method and the system facilitate the use of kinetic parameters as a single variable (e.g., reactivity) for source rock evaluation and characterization. To this end, the method and the system provide a new scheme to improve selection and assignment of kinetic parameters in basin modeling.

In one or more embodiments, fundamentals of source rock kinetics for the implementation of the method and the system include an Arrhenius equation and kinetic parameters, a derivation of kinetic parameters from pyrolysis experiments, and using of kinetic parameters in basin modeling and source rock evaluation. To this end, the method and the system are based on the principles of conversion of kerogen to petroleum in source rock, which are regarded as a series of irreversible reactions controlled by first-order chemical kinetics. These chemical kinetics may be described by the Arrhenius equation in equation (1). Equation (1) determines the rate of the transformation of kerogen to hydrocarbon under thermal stress during burial history of a source rock, and demonstrates an effect of temperature and time on petroleum generation. The kinetic parameters, activation energy Ea and frequency factor A, are critical inputs for a source rock in basin modeling to quantify generation, retention, and expulsion of petroleum and to determine the timing of any associated processes.

$$k = Ae^{-E_a/RT} \qquad (1)$$

In equation (1), k is a reaction rate describing a change in molar mass of a reactant with respect to time; A is the frequency factor (i.e., pre-exponential) describing a number of potential elementary reactions per unit of time; Ea is the activation energy defined as the energy barrier that must be exceeded in order for a reaction to occur; R is a gas constant equal to 8.31447 (i.e., measure in Ws/mol/K); and T is a reaction temperature (i.e., measure in Kelvin or K).

In one or more embodiments, thermal reactivity of source rock (i.e., thermal stability of kerogen) is a critical variable to determine the extent of kerogen transformation and the timing of hydrocarbon generation in geological history. In some embodiments, the reactivity is considered with other parameters like TOC (i.e., quantity), kerogen type (i.e., quality), and $T_{max}$ or vitrinite reflectance (i.e., maturity) to fully characterize a source rock.

Advantageously, the method and the system described herein provide a streamlined solution to evaluate the reactivity of source rock. The method and the system allow formats of commonly used kinetic parameters to be directly compared and interpreted. In this case, the reactivity of source rock may not need to be evaluated in kinetics analysis or basin modeling software by a geochemist or basin modeler that is expected to be familiar with kinetic analysis and maturation modeling. The method and the system expand the use of reactivity in source rock evaluation and shale resource assessment by preventing expertise and/or access to proper software limit source rock evaluation.

Further, the method and the system described herein improve the practice of basin modeling by addressing the heterogeneity of source rock (i.e., the kinetics of source rock may change vertically and laterally in a source rock) and by providing a well-grounded approach to assign measured kinetic parameters derived from immature source rock units to matured source rock units in a sedimentary basin.

In one or more embodiments, the method and the system include weighting an average Ea (i.e., also referred as WA-Ea) to simplify the format of Ea for discrete distribution. Further, the method and the system may include a cross-plot of WA-Ea and log (A) to evaluate reactivity and rank reactivities for source rock without needing kinetics or basin modeling software. The method and the system may include implementing a process to transfer kinetic parameters to reactivity as a single variable for source rock evaluation and characterization. The method and the system may include developing a scheme to assign kinetic parameters in basin modeling based on the ranking of reactivities.

In some embodiments, evaluating reactivity for source rock evaluation according to the method and the system may include determining thermal reactivity (i.e., chemical reactivity under thermal stress) of source rocks at a same level of thermal maturity. The method and the system may include interpreting kinetic parameters derived from thermally mature source rock samples, which improves over methods and/or systems that only handle kinetic parameters derived from immature source rock samples. The method and the system may compare published, archived, and measured kinetic parameters of source rock samples. The method and the system may convert complex format of kinetic parameters into reactivity as a single variable source rock evaluation and characterization.

In some embodiments, ranking of reactivities for kinetics assignment in basin modeling according to the method and the system may include ranking thermal reactivities of source rock samples at different thermal maturities. The method and the system may include assigning kinetic parameters derived from immature source rock unit to mature source rock units in a source rock formation in basin modeling. The method and the system may evaluate reactivity to improve the selection and assignment of kinetic parameters in basin modeling.

In one or more embodiments, the method and the system view thermal reactivity as a critical variable because the reactivity of source rock samples may be evaluated in kinetics analysis or basin modeling software by generating and comparing kerogen transformation curves. The method and the system may include optimized approaches over methods solely relying on parameters such as depositional environment, stratigraphy, and kerogen type. The method and the system may include optimized approaches over schemes such as gross depositional and stratigraphic age that define five organofacies and assign each organofacies with a predetermined average kinetics from a suite of source rocks in the organofacies. The method and the system may include optimized approaches over measuring as many possible kinetics for immature samples as possible to constrain uncertainties by using the average distribution Ea, the average A, and the standard deviations of Ea in numerical simulation. The method and the system may provide the awareness and quantification of uncertainties in kinetics modeling while providing guidance for kinetics assignment.

In one or more embodiments, the method and the system may include optimized approaches over applying kinetics determined at each location for a limited part of a study area because there is no specific guidance to constrain the study area and stratigraphic unit where the kinetics can be applied. The method and the system may include optimized approaches over solely using a weighted-average method where kinetic parameters for samples from different locations and depths in the source rock interval are combined by giving the distribution Ea for each sample a weight proportional to its Rock-Eval S2 yield. In particular, while the single merged kinetics captures the averaged transformation and the gross potential of the source rock, this approach losses the characteristics of timing, potential, and composition, (e.g., if it is multi-component kinetics) of different source rock units (i.e., the heterogeneity of a source rock).

In one or more embodiments, the method and the system provide kinetic parameters from either kinetic measurement on source rock samples or collecting from publications for the evaluation. In particular, the reactivities of source rocks may be compared by transformation curves that are generated in kinetics analysis or basin modeling software by extrapolating kinetic parameters with a geological heating rate. In this regard, the method and the system do not require commercialized modeling software for the evaluation of source rock reactivity because the method and the system simplify the complex format of kinetic parameters (i.e., WA-Ea and A) and graphically show these parameters on a cross-plot, which facilitates geologists and explorationists to use kinetic parameters for source rock evaluation.

In one or more embodiments, the method and the system provide a scheme to assign measured kinetics based on the ranking of reactivities which may be used as a basis for developing new methods and/or new systems for organofacies mapping and stratigraphy correlation.

The method and the systems may be used by oil companies and technical service providers to enhance evaluation (e.g., characterization) of source rocks of conventional petroleum systems, as well as source-rock reservoir (e.g., unconventional petroleum systems). The method and the systems may compare kinetic parameters and provide evaluation of source rock reactivity, which may create more value of kinetic analysis. To this end, the method and the systems may improve the classification of kinetic parameters and the selection and assignment of kinetics in basin modeling software.

FIG. 1 shows a schematic diagram illustrating a collecting tool 160 used for retrieving a source rock sample 150 from an underground sediment section 130 at a collecting site 100. The collecting tool 160 includes a central chamber 140 configured to collect, contain, and transport the source rock sample 150. The collecting tool 160 may have a cylindrical housing that extends through the entire length of the collecting tool 160 along a central axis 180. The collecting tool 160 may be lowered and raised along the underground sediment section 130 to sample source rocks. The collecting tool 160 may be lowered to a depth between an upper sediment section 110 and a lower sediment section 170 using a conveyance mechanism 120. In some embodiments, the collecting tool 160 includes a top portion operably connected to a conveyance mechanism 120 that lowers and rises the collecting tool 160 along the upper sediment section 110, the underground sediment section 130, and the lower sediment section 170. In some embodiments, the upper sediment section 110, the underground sediment section 130, and the lower sediment section 170 may spawn equal or different lengths of depth. In some embodiments, the upper sediment section 110, the underground sediment section 130, and the lower sediment section 170 may be equal or different types of source rock samples having equal or similar maturities.

In some embodiments, the collecting tool 160 may exchange information with a control system 360 (i.e., surface panel). In some embodiments, the collecting tool 160 may include sensors and systems for collecting data relating to the area of interest. In some embodiments, the collecting tool 160 may include hardware and/or software for creating a secure wireless connection (i.e., a communication link) with the surface panel to insure real-time data exchanges and compliance with data protection requirements.

Figure 2:
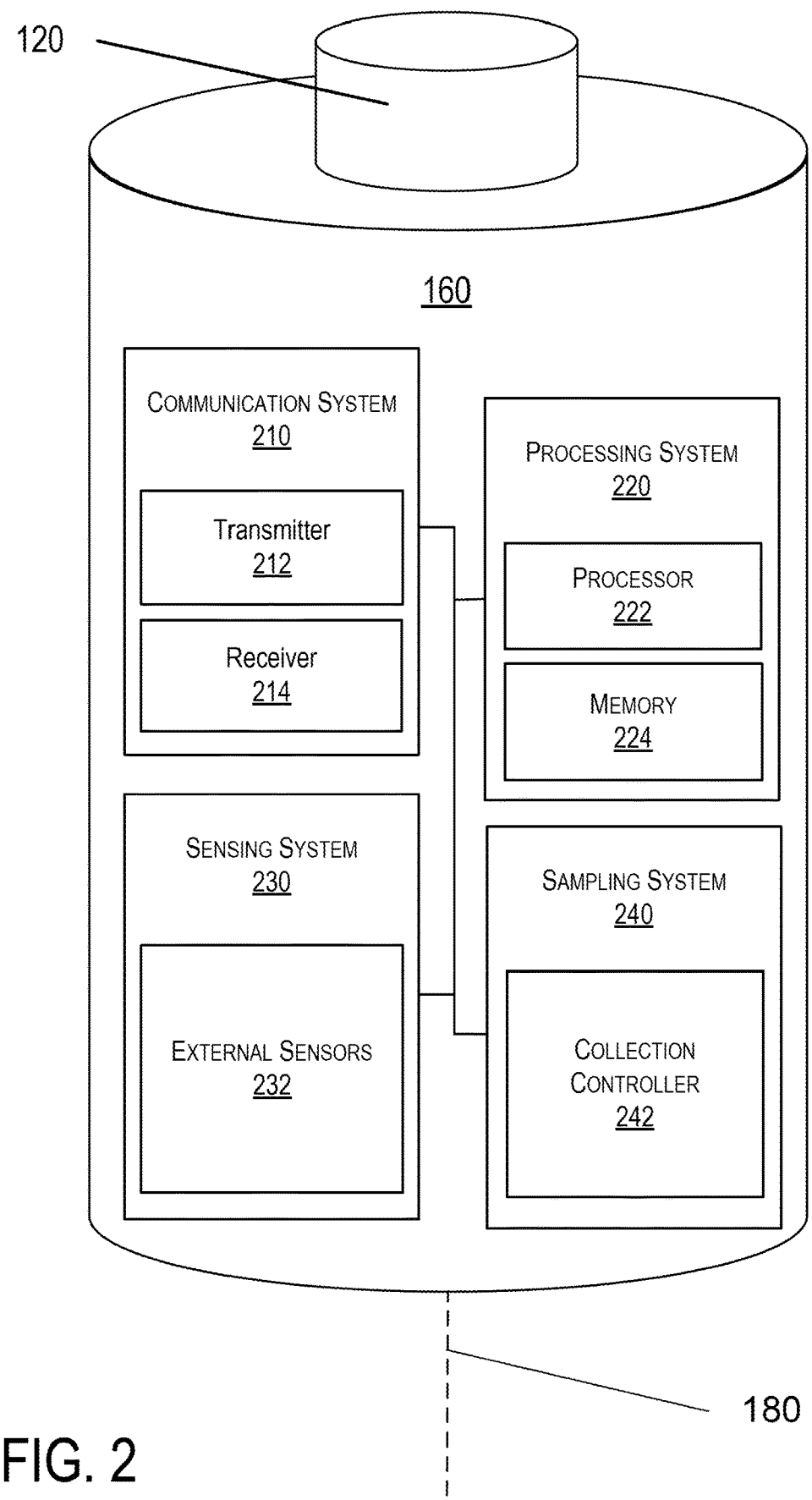
FIG. 2 shows a schematic diagram of a collecting tool in accordance with one or more embodiments.

FIG. 2 shows a schematic diagram showing various systems that may be incorporated into the collecting tool 160. In some embodiments, the collecting tool 160 includes electronic components that enable the collecting tool 160 to perform communication functions, data collecting functions, and/or processing functions. In some embodiments, the collecting tool 160 includes a communication system 210, a processing system 220, a sensing system 230, and a sampling system 240 coupled to the central chamber 140 containing the source rock sample 150. The communication system 210 may include communication devices such as a transmitter 212 and a receiver 214. The transmitter 212 and the receiver 214 may transmit and receive communication signals, respectively. Specifically, the transmitter 212 and the receiver 214 may communicate with one or more control systems located at a remote location through a wired connection. In some embodiments, the communication system 210 may communicate wirelessly with the control system 360 located at the surface 370. The surface 370 may be an underwater surface.

The processing system 220 may include a processor 222 and a memory 224. The processor 222 may perform computational processes simultaneously and/or sequentially. The processor 222 may determine information to be transmitted and processes to be performed using information received or collected. Similarly, the processor 222 may control collection and exchange of geospatial information from the collecting tool 160.

The sensing system 230 may include external sensors 232. The external sensors 232 may be sensors that collect physical data from the environment surrounding the collecting tool 160. The external sensors 232 may be lightweight sensors requiring a small footprint. These sensors may exchange information with each other and supply it to the processor 222 for analysis. The external sensors 232 may be logging tools of an electrical type, a nuclear type, a sonic type, or another type. The external sensors 232 may release signals (i.e., electrical, nuclear, or sonic) through a signal generator at a sensing portion.

The sampling system 240 may include a collection controller 242 that coordinates collection of the source rock sample 150 through a central aperture (not shown) at the bottom of the collecting tool 160. Coordinating collection of the source rock sample 150 may include determining the filling of the central chamber 140 at a predetermined depth or determining a parameter of the source rock sample 150 collected at the underground sediment section 130.

Figure 3:
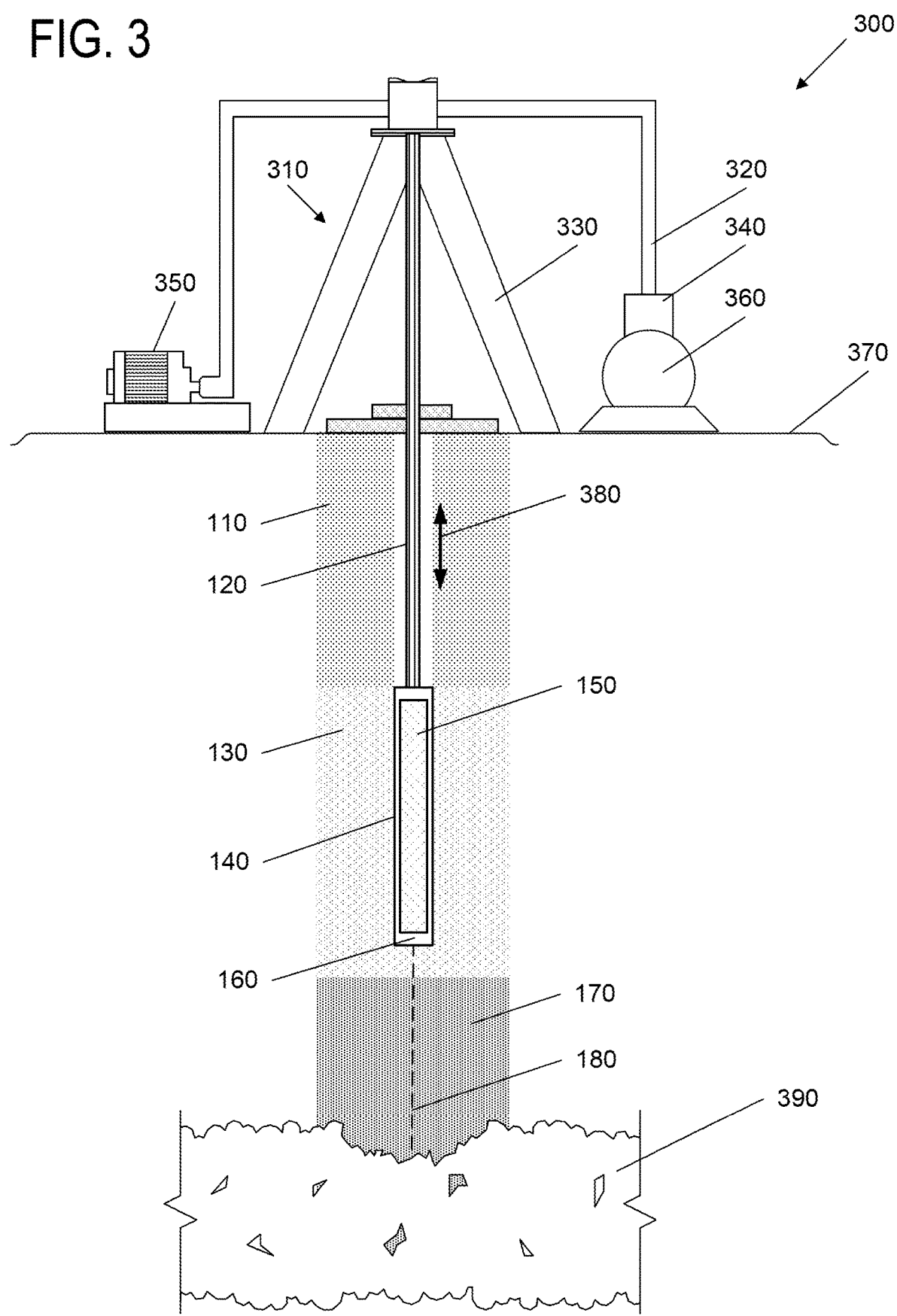
FIG. 3 shows a source rock sampling procedure in accordance with one or more embodiments.

FIG. 3 shows an example of the collecting tool 160 being used for collecting the source rock sample 150 in accordance with one or more embodiments. The collection system 300 may include surface equipment 310 including actuating devices 350, sensors 340, and the control system 360 connected to one another using hardware and/or software to create interfaces 320. Further, the collection system 300 may be propped by structures 330 from the surface 370. The collection system 300 includes the upper sediment section 110, the underground sediment section 130, and the lower sediment section 170 extending from the surface 370 to an underground formation 390. The underground formation 390 may have porous areas including hydrocarbon pools. In some embodiments, the collecting tool 160 is translated in a vertical direction 380 using the surface equipment.

The collection system 300 may include the control system ("control system") 360. In some embodiments, during operation of the collection system 300, the control system 360 may collect and record wellhead data for the collection system 300. In some embodiments, the control system 360 may regulate the movement of the conveyance mechanism 120 by modifying the power supplied to the actuating devices 350. The conveyance mechanism 120 may be a tool coupling the collecting tool 160 to the structures 330. In some embodiments, the control system 360 includes the surface panel described in reference to FIG. 1.

The control system 360 may include a laboratory equipment room (not shown). The laboratory equipment room may include hardware and/or software with functionality for generating one or more basin models regarding the formation 390 and/or performing one or more reservoir simulations. The laboratory equipment room may be used for performing experiments relating to identifying kinetic parameters in a source rock sample associated to the underground sediment section 130. Further, the laboratory equipment room may include a memory device for storing formation logs and data regarding source rock samples for performing modeling or simulations. While the laboratory equipment room may be coupled to the control system 360, the laboratory equipment room may be located away from the site. In some embodiments, the laboratory equipment room may include a computer system disposed to estimate a depth of the collecting tool 160 at any given time. The laboratory equipment room may use the memory for compiling and storing historical data about the underground sediment section 130.

In some embodiments, the actuating devices 350 may be motors or pumps connected to the conveyance mechanism 120 and the control system 360. In some embodiments, the measurements are recorded in real-time, and are available for review or use within seconds, minutes or hours of the condition being sensed (e.g., the measurements are available within 1 hour of the condition being sensed). In such an embodiment, the wellhead data may be referred to as "real-time" wellhead data. Real-time data may enable an operator of the collection system 300 to assess a relatively current state of the collection system 300, and make real-time decisions regarding development of the collection system 300 and the reservoir.

Figure 4:
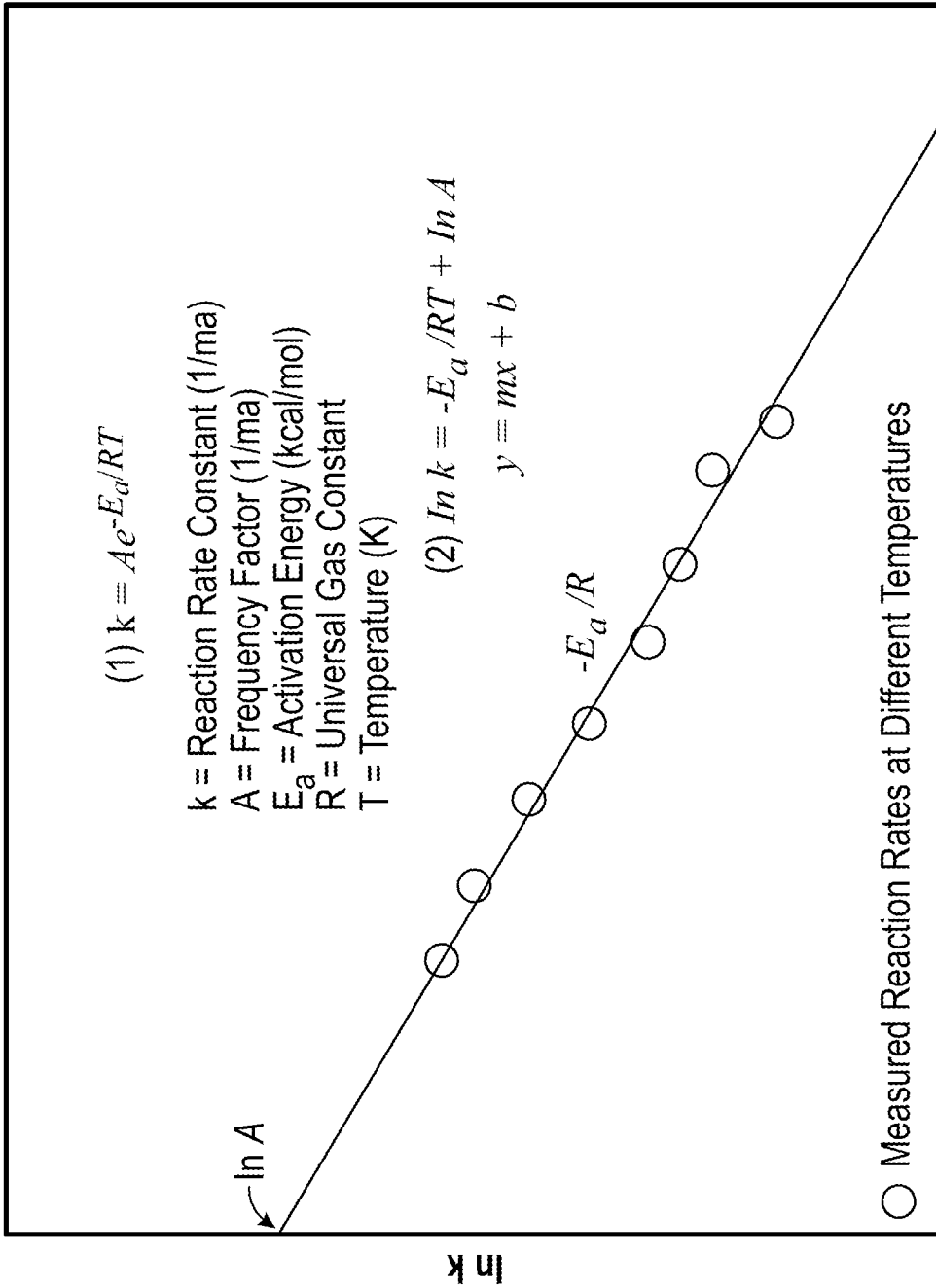
FIG. 4 shows a plot using measured reaction rate (k) and temperature to determine kinetic parameters (Ea and A) for Arrhenius Equation in accordance with one or more embodiments.

FIG. 4 shows an example of a plot according to one or more embodiments. The relationship between reaction rate k and temperature T in kerogen transformation is described by Arrhenius equation (1). The reaction rate k represents a linear positive relationship with temperature in a logarithmic scale. Higher temperature and lower Ea favor fast transformation rates k for reactions. As shown in FIG. 4, the plot illustrates the measured reaction rate k, which may be inverted into Ea and A pairs by a regression line in a plot showing "1/T vs. ln(k)." Based on this relation, one or more embodiments obtain kinetic parameters from pyrolysis experiments. Determination of kinetic parameters for kerogen transformation is a two-step process consisting of artificial maturation experiments followed by fitting of calculated kinetic parameters to the laboratory data.

Figure 5:
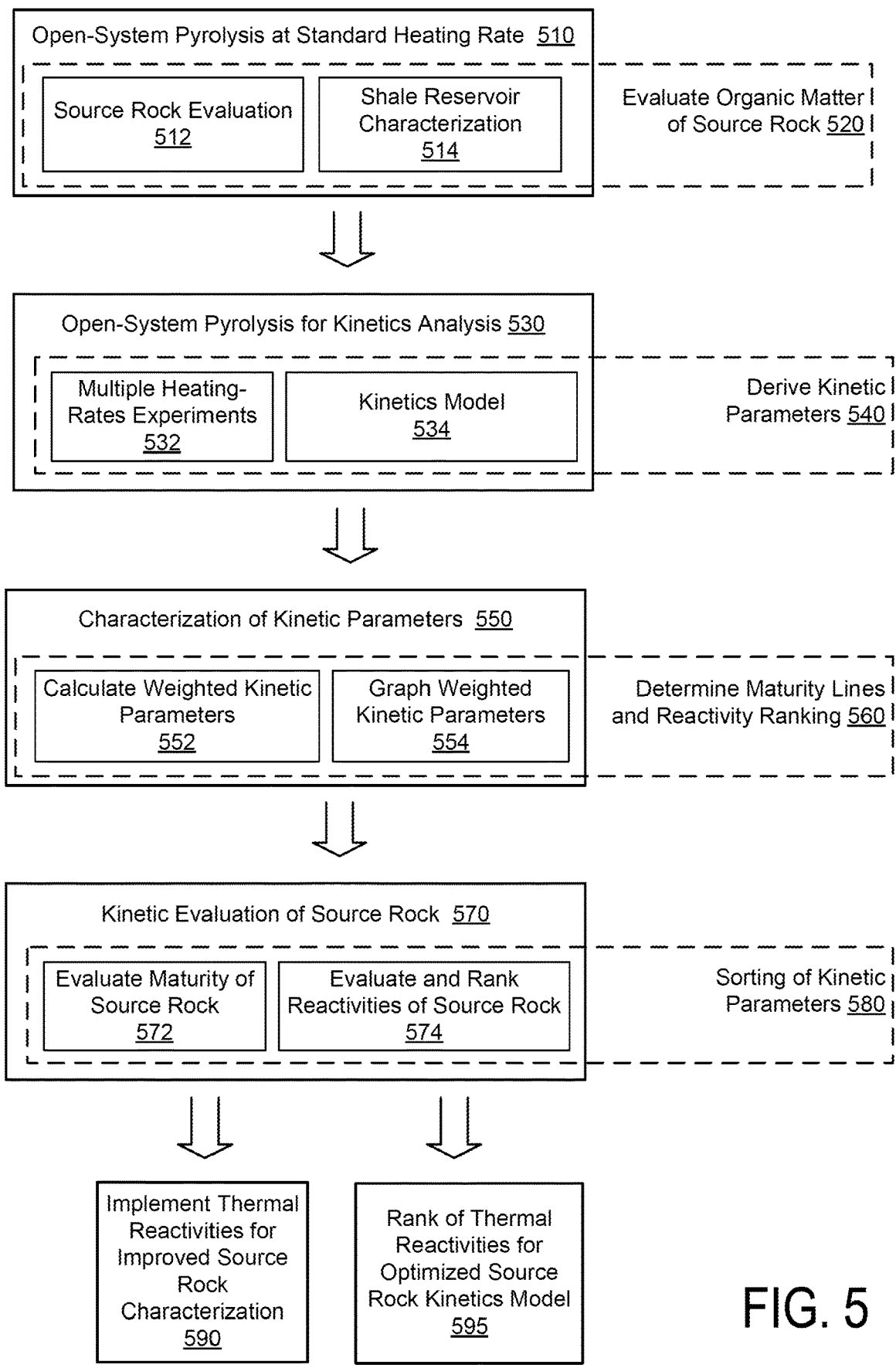
FIG. 5 shows a schematic diagram of a system in accordance with one or more embodiments.

FIG. 5 shows a schematic diagram for an example in accordance with one or more embodiments. In one or more embodiments, the method and the system include a new scheme for processing kinetic parameters and for interpreting the kinetic parameters on a cross-plot graph. The method and the system may process measured kinetic parameters or re-process published/archived kinetic parameters, without the use of kinetics analysis or basin modeling software while providing a quick assessment on reactivity of source rocks.

In some embodiments, open-system pyrolysis using a standard heating rate 510 relies in source rock samples to evaluate organic matter of a source rock 520 (richness, quality, and maturity) for source rock evaluation 512 and shale reservoir characterization 514. In some embodiments, the open-system pyrolysis at the standard heating rate 510 is a scheme to use pyrolysis experiments to obtain TOC and Rock-Eval parameters for evaluating source rock samples and bulk kinetic parameters to improve source rock evaluation and basin modeling.

In some embodiments, a temperature-programmed open-system pyrolysis, such as Rock-Eval, HAWK, SR Analyzer, POPI-TOC and Pyromat, may be used for source rock evaluation 512 and shale reservoir characterization 514. Pyrolysis experiments performed with a standard heating rate (i.e., 25° C./min) provide basic parameters (including TOC, S1, S2, S3, $T_{max}$, HI, OI, and PI) to quantify richness, quality, and maturity of organic matter in source rock. The pyrolysis experiments may be conducted with multiple heating rates, commonly using the rates in the range from 0.5° C./min to 50° C./min, to generate pyrolysis data recording yield of pyrolysis, temperature, and time. The pyrolysis data then may be processed in kinetics analysis software (e.g., Kinetics2000, Kinetics05, Kinetics2015) or manual regression and parameter fitting (as shown in FIG. 4) to derive kinetic parameters.

In particular, finely ground source rock with good organic richness (i.e., TOC>1%) or isolated kerogen samples may be used in pyrolysis experiments for kinetic analysis. The standard pyrolysis for kinetics may require thermally immature, to marginally mature, samples (i.e., vitrinite reflectance (Ro)<0.6%), which allow obtained kinetic parameters to be used in basin modeling to simulate hydrocarbon generation from the inception of kerogen transformation to the exhaustion of all kerogen potential. In some embodiments, the method and the system may be applied on the mature samples, as long as the mature samples may generate hydrocarbon response (such as an S2 peak) in pyrolysis, to evaluate and to compare their reactivities.

In some embodiments, different mathematical models may be used in kinetics analysis to derive kinetic parameters for different chemical reactions. A variety of mathematical models, including Discrete, Gaussian, Nucleation, 1st or Nth Order, Weibull, Alternate Pathway, and Isoconversional, may be implemented using software. In some embodiments, the model and the system may be configured to process commonly used model for kerogen decomposition, the Discrete model—an Ea distribution with an energy spacing of 1 kcal/mol, and one optimized A. Other models with a continuous Ea distribution and one A may also be processed. In this regard, the method and the system may include calculating the weighted average values WA-Ea and evaluating re-processed kinetic parameters on WA-Ea vs. A cross-plots.

In some embodiments, open-system pyrolysis for kinetics analysis 530 include multiple heating-rates experiments 532 and applying mathematical models of kinetics 534 to derive kinetic parameters 540. Source rock evaluation by standard open-system pyrolysis may include conducting open-system pyrolysis with a standard heating rate 510 and oxidation on whole rock powder samples to determine the TOC and the Rock-Eval parameters. In some embodiments, the kinetic analysis by multiple-heating-rates pyrolysis may include conducting the open-system pyrolysis experiments using multiple heating rates 534 (i.e., at least two heating rates which may differ by one or two orders of magnitude, such as 3° C./min and 30° C./min) on source rock samples. The source rock samples may be whole rock powder (i.e., TOC>1%) or isolated kerogen. The source rock samples may have variable maturities. In some embodiments, using a same pyrolysis instrument may allow different heating rates and sample types in an evaluation project to minimize the effects of laboratory and sample conditions on the determination of kinetic parameters.

In one or more embodiments, deriving kinetic parameters 540 using the pyrolysis data obtained from the open-system pyrolysis at the standard heating rate 510. In some embodiments, the pyrolysis data may be used to derive kinetic parameters 540 based on a mathematical model with an Ea distribution and a common A. In some embodiments, using a same kinetic analysis software (or a manual calculation method) and the same mathematical model (e.g., Discrete) in an evaluation project may ensure that the obtained kinetic parameters are comparable.

In some embodiments, characterization of kinetic parameters 550 includes calculating weighted kinetic parameters 552 and graphing weighted kinetic parameters 554 to determine maturity lines and reactivity ranking 560. The method and the system may assess and compare published, archived, and measured kinetic parameters. The comparison of published/archived/measured kinetics may require that the kinetic parameters are obtained by a same mathematical model (e.g., Discrete) and very similar laboratory techniques (e.g., open-system pyrolysis with similar minimum and maximum heating rates).

For a very thick source rock formation in a well or any area of interest, the kinetics data may be divided into sub-groups based on depth and rock properties to ensure the variation of Ro (vitrinite reflectance) or VRE (Ro equivalent) to be small enough (e.g., less than 0.1%) in each sub-group. At this point, $T_{max}$ results from the open-system pyrolysis 510 may be used to estimate the VRE and make trend lines for each sub-group.

In one or more embodiments, for a dataset that cannot be grouped by wells (e.g., scattered kinetic parameters from publications), the data into maturity groups may be divided (e.g., <0.5%, 0.5~0.6%, 0.6~0.7%, . . . ) and then make trend lines for each maturity group.

Figure 8:
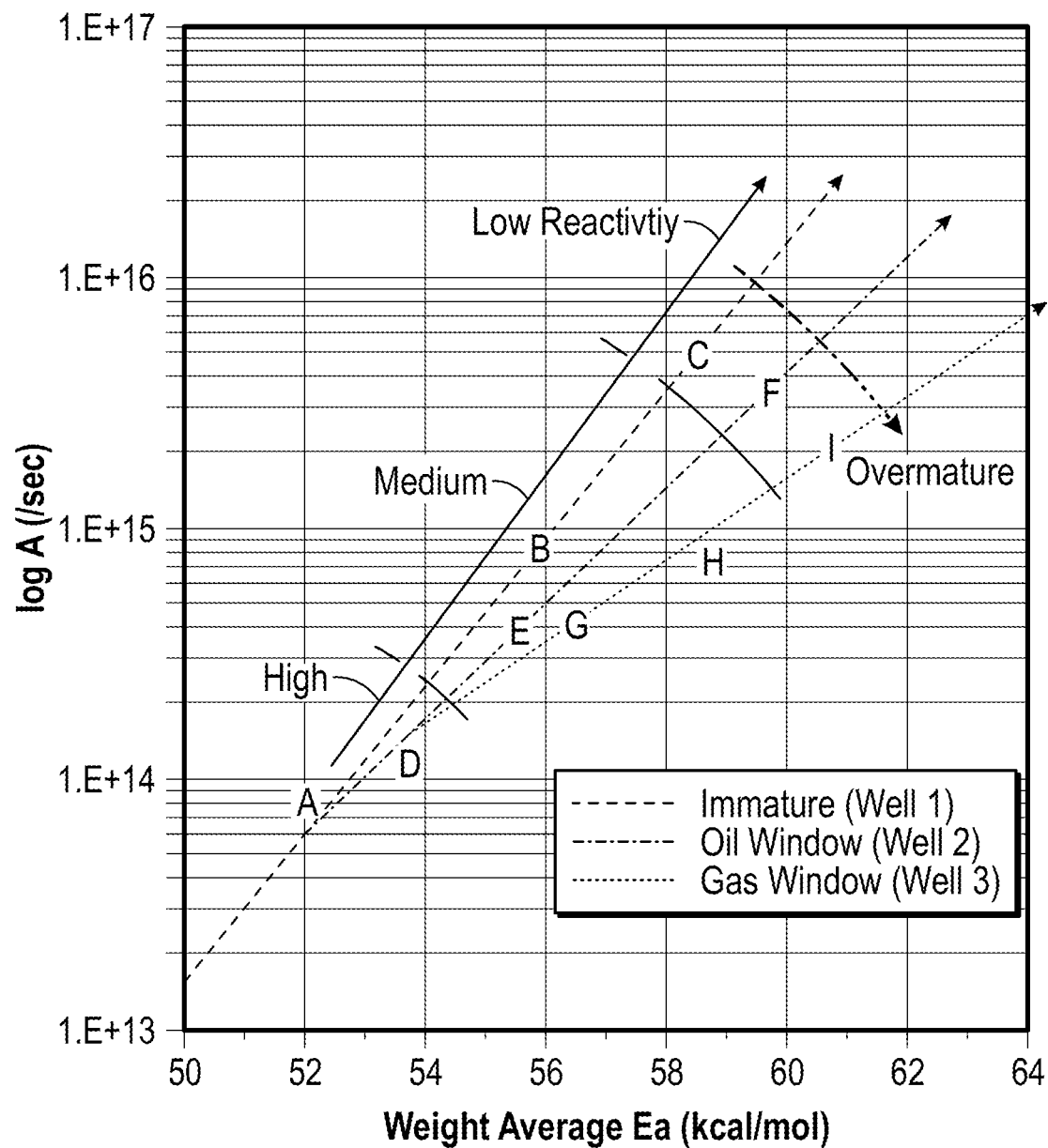
FIG. 8 shows a plot including one or more kinetic parameters reprocessed by the method in accordance with one or more embodiments.
Figure 11A:
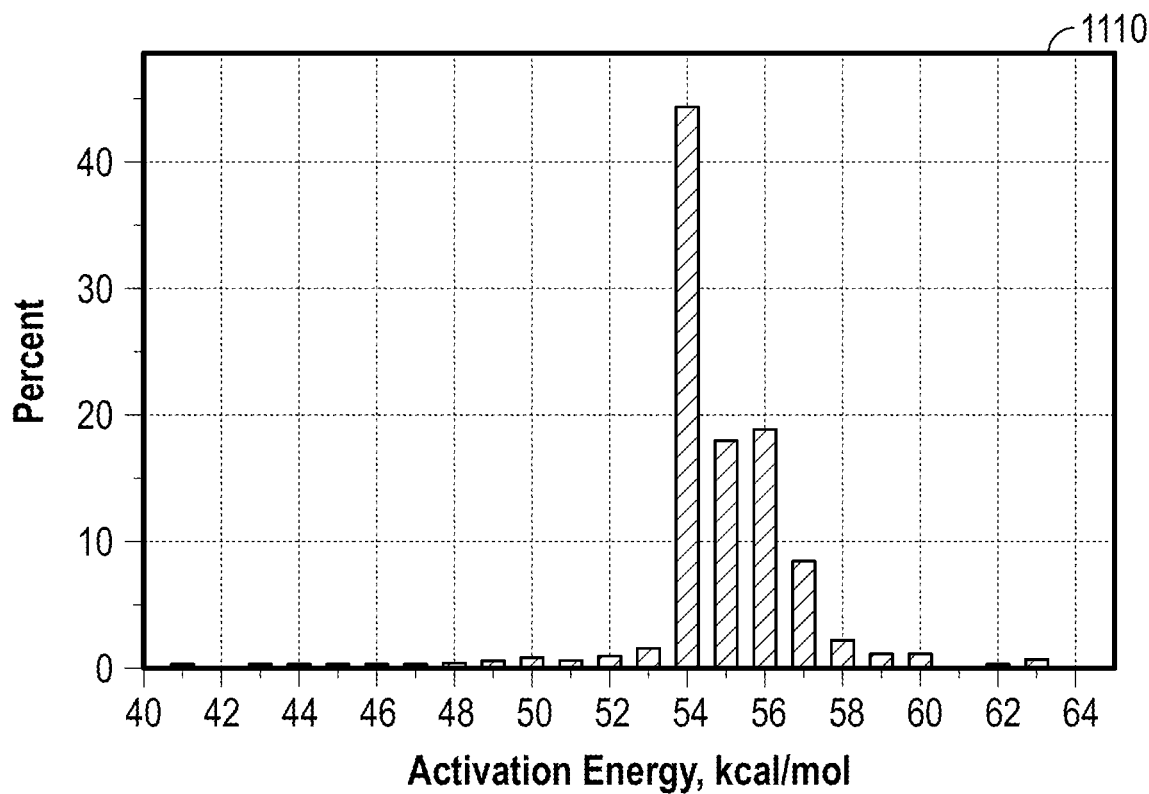
FIGS. 11A-11D show graphs for examples of common-used kinetic parameters in accordance with one or more embodiments.
Figure 11B:
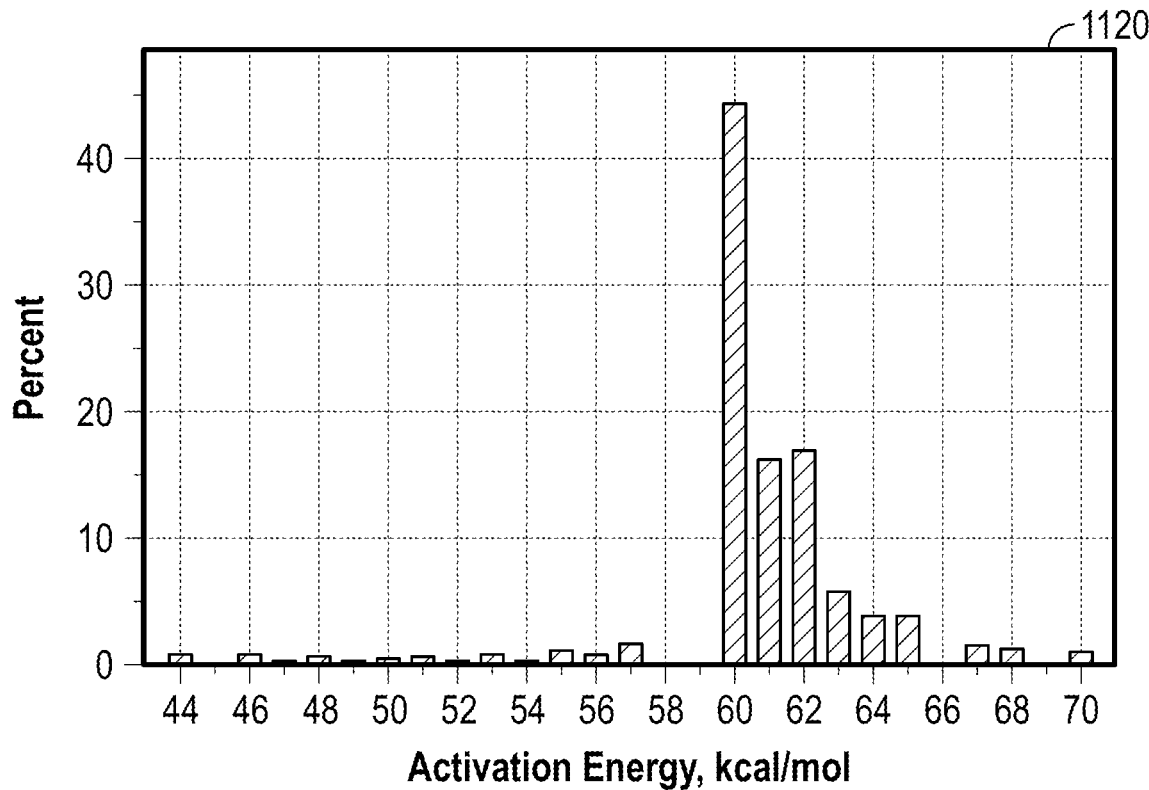
Figure 11C:
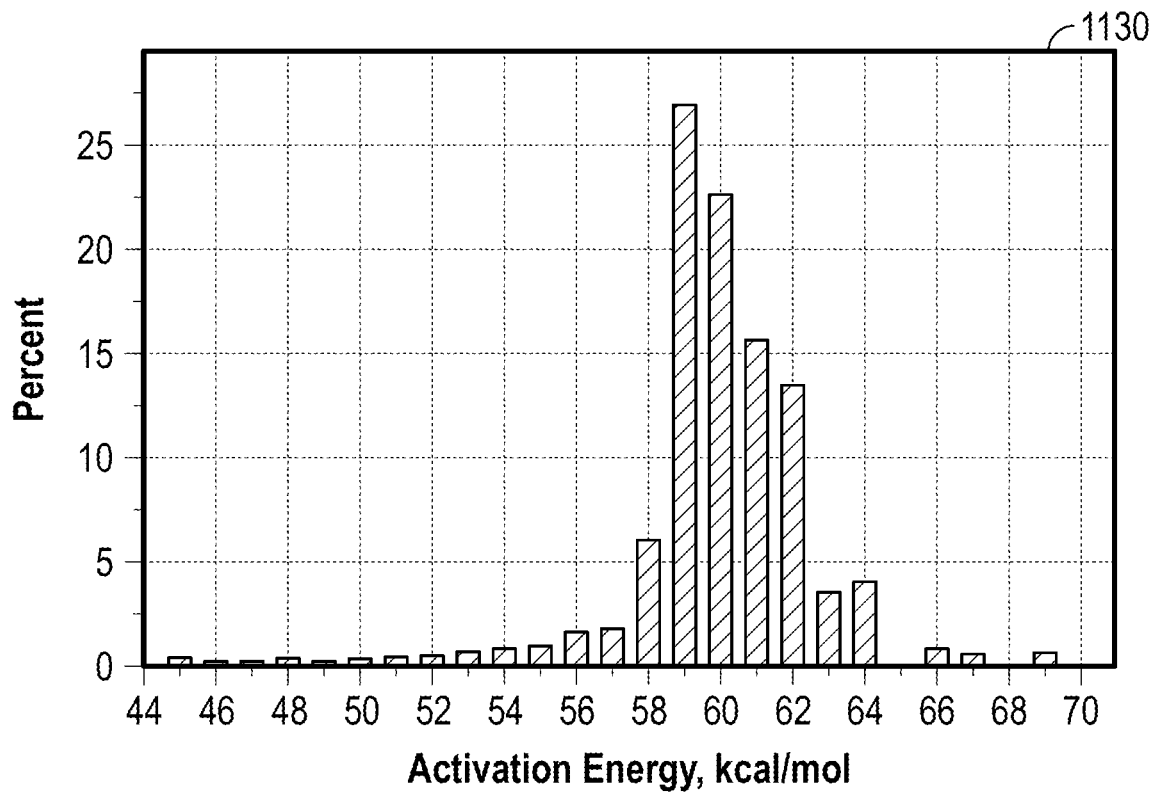
Figure 11D:
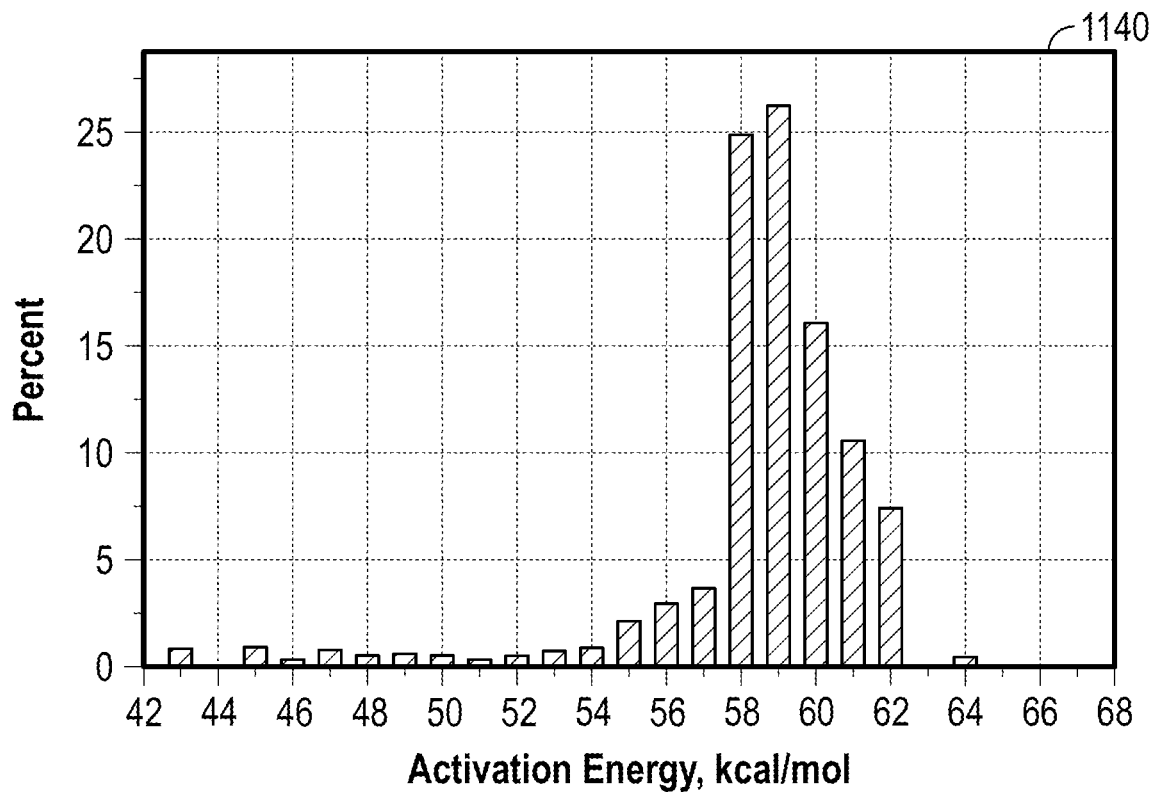

In one or more embodiments, maturity lines can be determined on a cross-plot to show a clockwise increase of maturity as shown in the examples discussed under FIG. 8, where there is a systematic shift in Ea distribution with increasing maturity.

In some embodiments, kinetic evaluation of source rock 570 includes evaluating maturity of source rock 572 and evaluating and ranking reactivities of source rock 574 to sort kinetic parameters 580. In evaluating maturity of source rock, an arc arrow with gradient colors may indicate a direction of increasing maturity. The maturity of a new source rock sample therefore may be qualitatively estimated based on the respective WA-Ea and A values. In evaluating and ranking reactivities for source rock samples, arrows may indicate a direction for decreasing reactivity. The reactivities of source rock samples with similar maturities (e.g., Ro variation <0.1%) or from a source rock formation in a well may be determined based on a specific trend line.

Implementing thermal reactivity for improved source rock characterization 590 may include providing a new variable or dimension that is beyond the three parameters measured for source rock evaluation (i.e., quantity, quality, and thermal maturity). In this regard, the source rock samples with higher reactivity may start generating hydrocarbons and reach peak generation before the source rock with lower reactivity, even if the two source rock samples have the same kerogen type, TOC, HI, and thermal maturity. In another example, a shallower source rock with higher reactivity may generate hydrocarbons before a deeper source rock with lower reactivity.

In one or more embodiments, a graphic method provides a quick assessment of reactivity without complex calculation and basin modeling. In this regard, the independent assessment of reactivity may be added to source rock evaluation programs to better characterize a source rock and evaluate the hydrocarbon potential in a dynamically geological history.

In one or more embodiments, ranking of thermal reactivities for optimized rock kinetics model 595 may include optimizing source rock sample kinetics models in basin modeling. The kinetic parameters derived from an immature source rock sample may be used as a kinetic representative for the whole source rock formation in a basin, which may then be used to simulate hydrocarbon generation and expulsion from the source rock in the petroleum system. The simplified kinetics model may assume that the kinetic parameters of an immature source rock do not change significantly. In some embodiments, the kinetics of immature source rock represent those of the more mature and deeper source rock.

Figure 6:
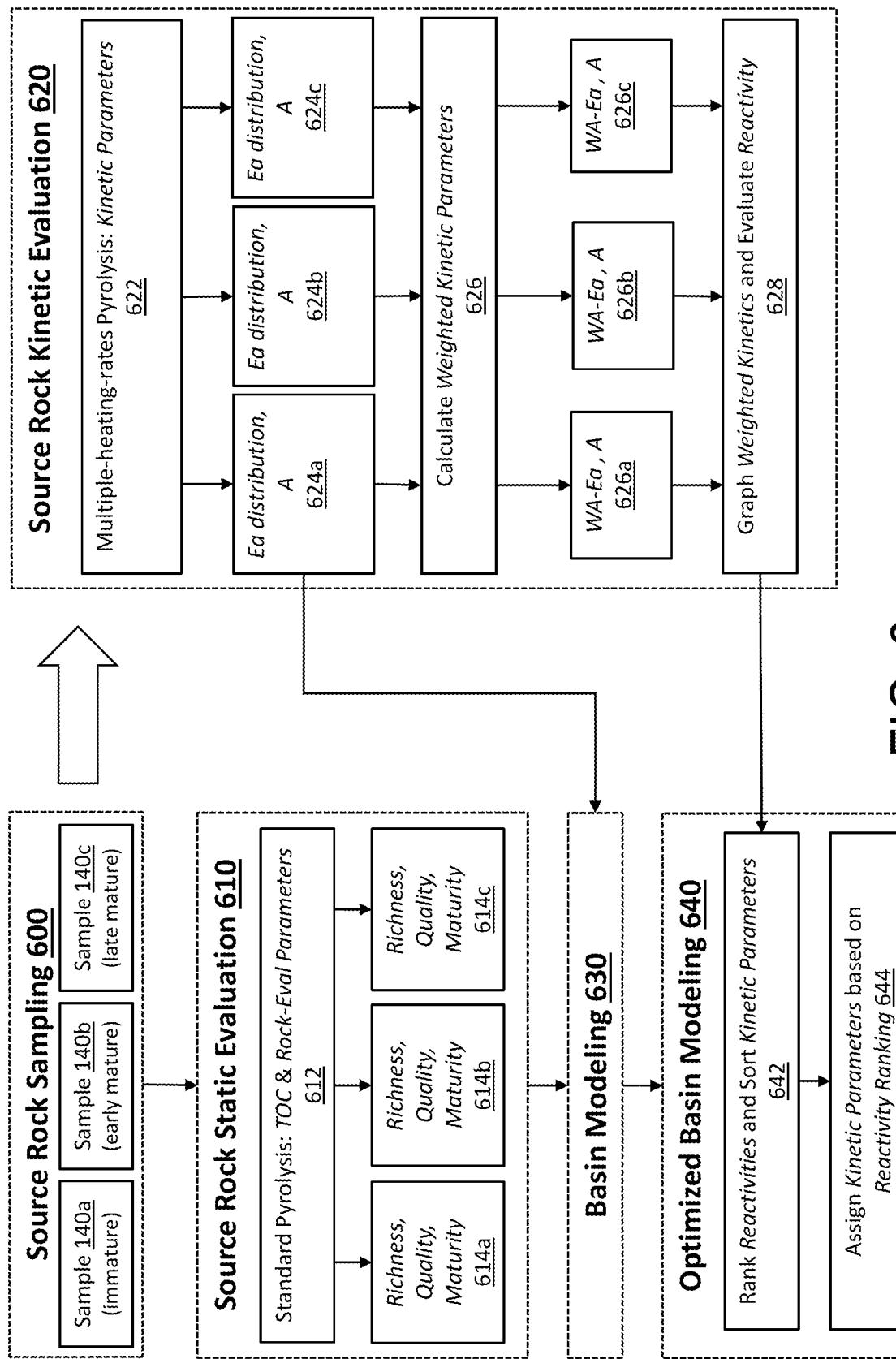
FIG. 6 shows a schematic diagram of a system in accordance with one or more embodiments.

FIG. 6 shows an example for processing source rock samples in accordance with one or more embodiments. FIG. 6 illustrates a parallel processing stage occurring simultaneously or in order as more than source rock sample 140 may be processed for modeling as a result of the source rock sampling 600. The source rock sampling 600 may be performed using the devices described in reference to FIGS. 1, 2, and 3. In some embodiments, the source rock sampling 600 may cause source rock static evaluation 610, basin modeling 620, source rock kinetic evaluation 630, and further optimized basin modeling 640. In particular, the source rock sampling 600 may include taking a sample of immature, early mature, and late mature source rocks in samples 140a-140c, respectively.

In some embodiments, during source rock static evaluation 610 by standard open-system, standard pyrolysis involving TOC and Rock-Eval parameters 612 may be used to obtain organic matter richness, quality, and maturities of various source rock samples (614a, 614b, and 614c). In particular, open-system pyrolysis (a standard heating rate, usually 25° C./min) and oxidation on whole rock powder samples may be conducted to determine TOC and Rock-Eval parameters (e.g., S1, S2, $T_{max}$, HI, OI . . . ). In this regard, the data may be used to evaluate the richness, quality and maturity of organic matter of source rock.

In some embodiments, to conduct basin modeling 630, the organic matter richness, quality, and maturities of various source rock samples (614a-614c) are used to define the source rock(s) in the area of interest. Kinetic parameters from source rock kinetic evaluation 620 is another critical input to simulate the conversion of kerogen into hydrocarbon in source rock for basin modeling. Various source rock samples (140a-140c) are processed through multiple heating-rates pyrolysis 622 to obtain the kinetic parameters corresponding Ea distributions/A 624a, 624b, and 624c. In particular, open-system pyrolysis experiments may be conducted using multiple heating rates (at least two heating rates which differ by one or two orders of magnitude, such as 3 and 30° C./min) on source rock samples. The samples may be whole rock powder (TOC>1%) or isolated kerogen. The samples may have variable maturities. The same pyrolysis instrument, heating rates, and sample type may be kept using in an evaluation project to minimize the effects of laboratory and sample conditions on the determination of kinetic parameters. At this point, the pyrolysis data may be used to derive kinetic parameters based on a mathematical model with an Ea distribution and a common A. The same kinetic analysis software (or a manual calculation method) and the same mathematical model (e.g., Discrete) may be kept in an evaluation project to ensure that the obtained kinetic parameters are comparable. In some embodiments, published/archived parameters may be accessed and compared. The comparison of published/archived/measured kinetics may require that the kinetic parameters are obtained by the same mathematical model (e.g., Discrete) and very similar laboratory techniques (e.g., open-system pyrolysis with similar minimum and maximum heating rates). In some embodiments, only kinetic parameters derived from an immature source rock sample is used in traditional basin modeling.

In some embodiments, to perform source rock kinetic evaluation 620, the various corresponding Ea distributions/A 624a-624c are processed by calculating weighted kinetic parameters 626 to obtain various values WA-Ea/A 626a, 626b, and 626c using Equation (2).

$$WA - Ea = \sum_{i=1}^{n} Ea_i W_i \quad (2)$$

In Equation (2), $Ea_i$ distribution is the Ea value at each energy spacing and $W_i$ is the weight (i.e., normalized fraction) of each $Ea_i$.

Further, a graph may be obtained using weighted kinetics and evaluate reactivity 628 as a result. In some embodiments, the source rock kinetic evaluation 620 involves using a new parameter. The new parameter may be a single variable for reactivity used in source rock evaluation beyond richness, quality, and maturity of organic matter. In the graph, all pairs of WA-Ea and A may be paired along a logarithmic scale on a cross-plot. Cross-plot examples will be discussed in reference to FIGS. 7 and 13. In the graph, the scale and the range of X and Y axes for the cross-plot might be adjusted to show all data in a real case.

In some embodiments, the graphed weighted kinetics and evaluated reactivity 628 are used to rank reactivities and to sort kinetic parameters 642. At this point, kinetic parameters may be assigned to specific graphed values based on reactivity ranking 644. In this regard, the assigned kinetic parameters based on reactivity ranking 644 may be used to obtain an optimized basin modeling 640. In some embodiments, the optimized basin modeling 640 involves using multiple kinetics. The multiple kinetics may be multiple kinetic parameters assigned to different source rock units in a source rock based on ranking of reactivities and sorting of kinetic parameters.

The kinetics data (WA-Ea and A) may be grouped for a source rock formation from a well, and an exponential trend line may be generated for the data. The maturity for the same source rock formation in a well may be quite similar, unless the formation is very thick (e.g., >500 ft) or there is evidence showing intrusion in the formation. The graph may be useful to evaluate maturities of samples for published/archived kinetics when their maturity data are not available. In the graph, the reactivities of source rock samples with similar maturities (e.g., Ro variation <0.1%) or from a source rock formation in a well may be determined based on a trend line generated from the date.

As noted above, the reactivity or rankings of reactivities may provide a new variable or dimension that is beyond three parameters measured for source rock evaluation (quantity, quality, and thermal maturity). For example, the source rock with higher reactivity may start generating hydrocarbons and reach peak generation before the source rock with lower reactivity, even if the two source rocks have the same kerogen type, TOC, HI, and thermal maturity. In another example, a shallower source rock with higher reactivity may generate hydrocarbons before a deeper source rock with lower reactivity. As a result, a quick assessment of reactivity is provided without complex calculation and basin modeling. The independent assessment of reactivity may be added to source rock evaluation programs to better characterize a source rock and evaluate the hydrocarbon potential in a dynamically geological history.

In some embodiments, evaluating the source rock sampling 600 is divided into one or more obtaining periods (i.e., collection period) and/or one or more processing periods (i.e., evaluation period). In the obtaining periods, data is obtained by various processing means using the samples 140a, 140b, and 140c. In the processing periods, processed data may be organized into one or more aggregated packets representing the kinetic parameters and the standard parameters in real time such that the static evaluation 610, the kinetic evaluation 620, the basin modeling 630, and the optimized basin modeling 640 may be constantly updated (i.e., performing source rock sampling evaluation over a period of time in real time).

Figure 7A:
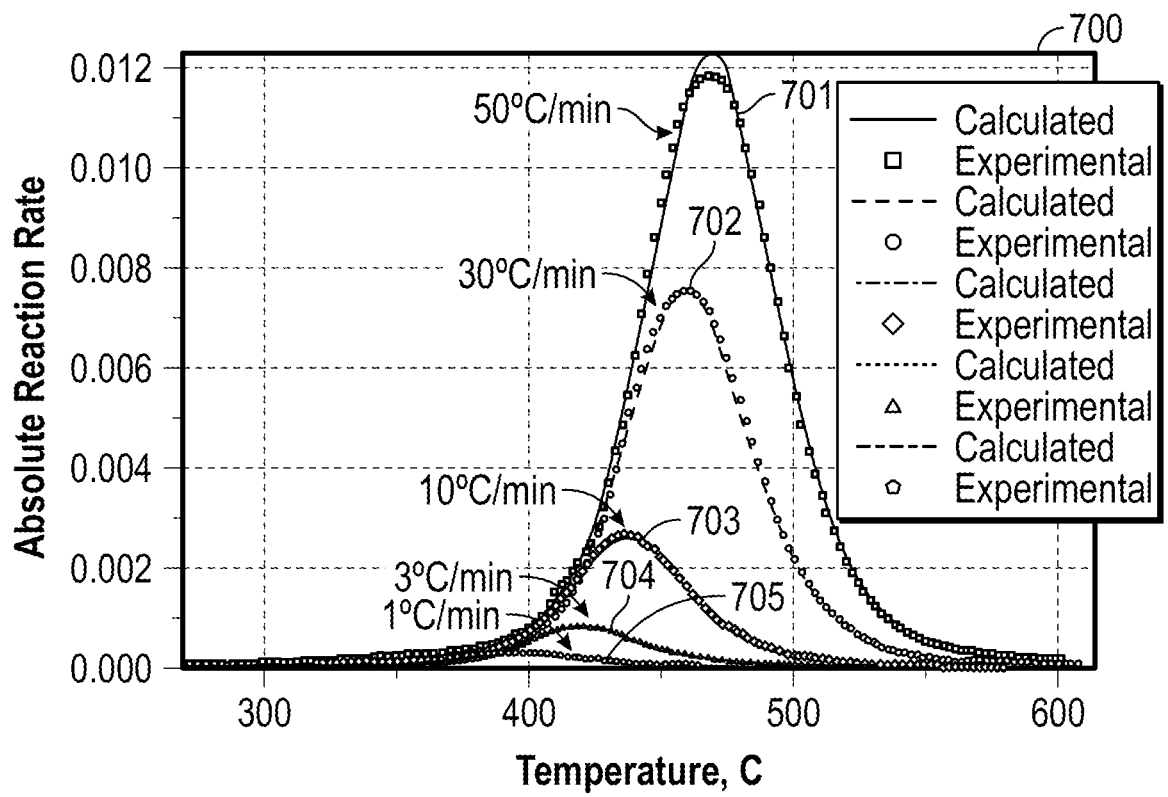
FIG. 7A shows a plot of reaction rates in pyrolysis experiments with different heating rates in accordance with one or more embodiments.
Figure 7B:
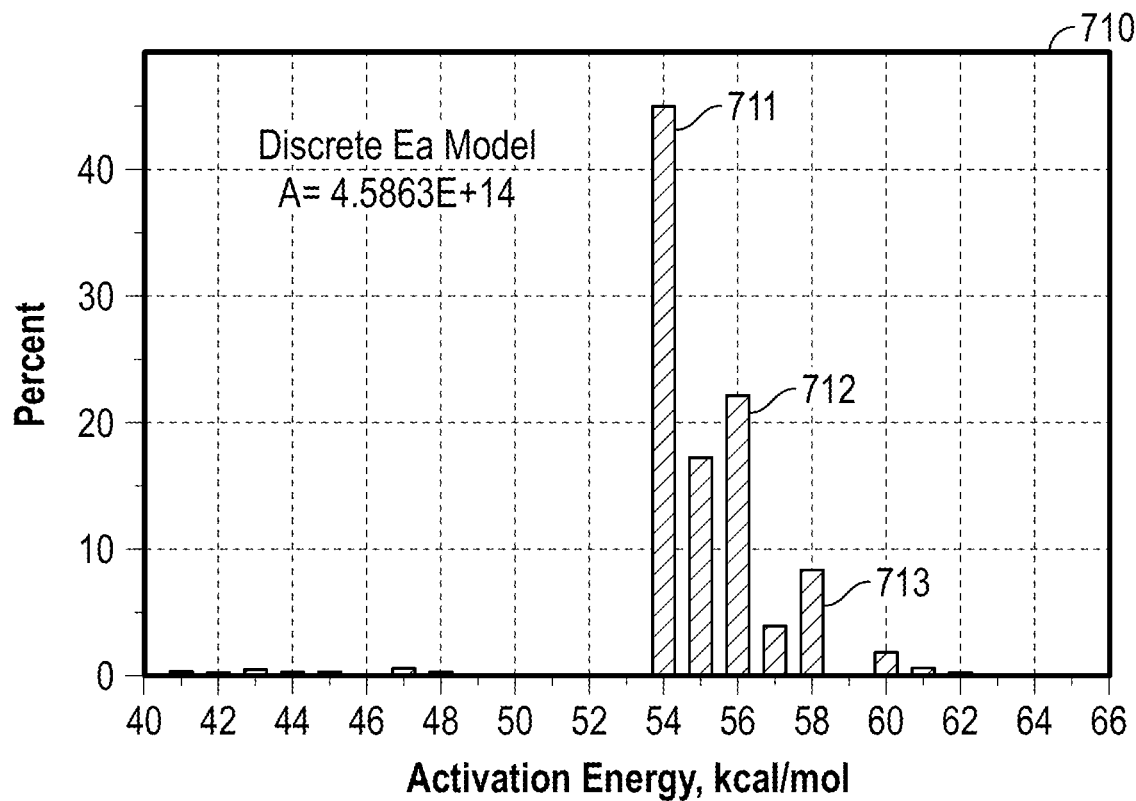
FIG. 7B shows a graph presenting one set of kinetic parameters in accordance with one or more embodiments.
Figure 7C:
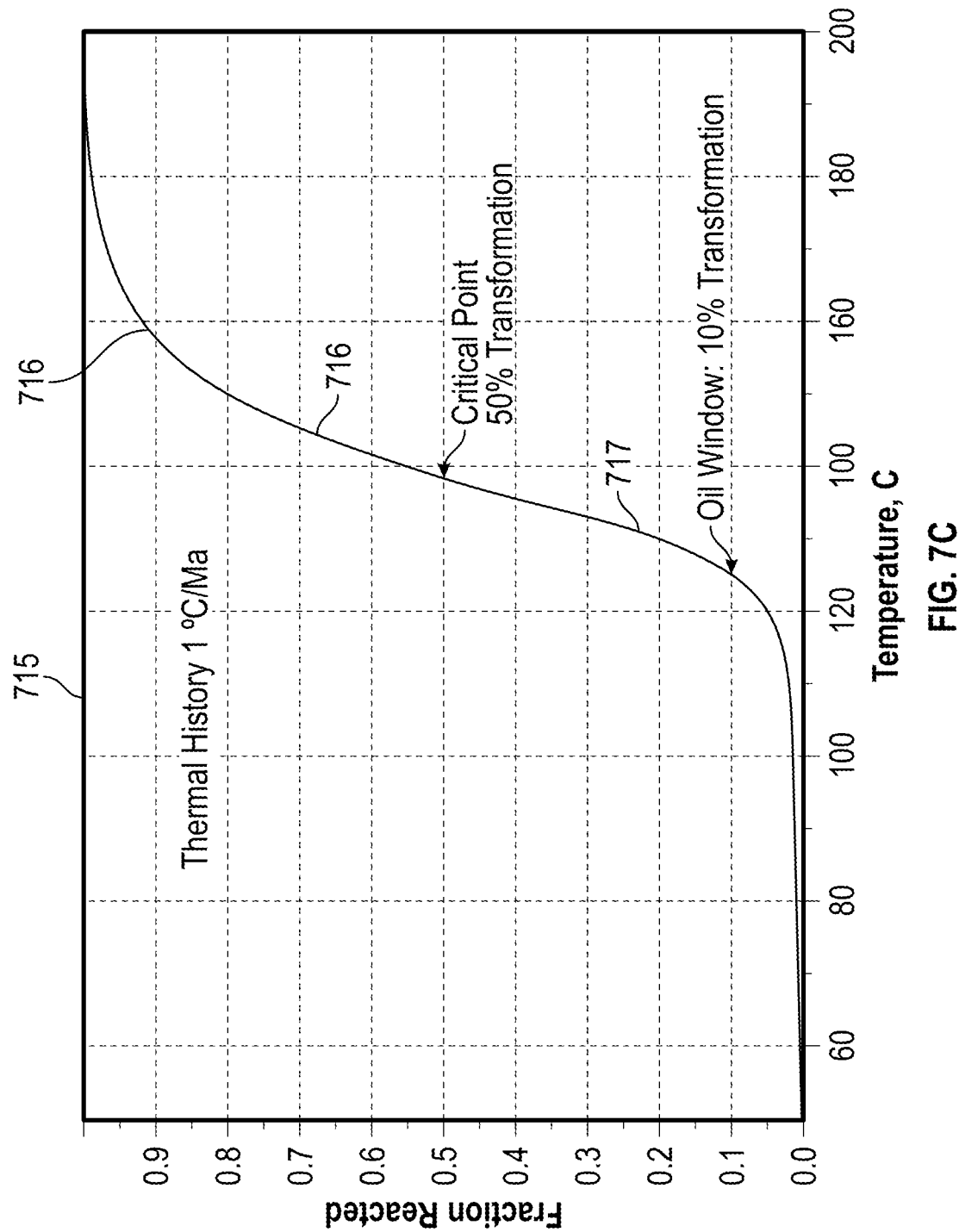
FIG. 7C shows a plot of transformation curve generated by applying kinetic parameters in an assumed thermal history in accordance with one or more embodiments.

FIGS. 7A, 7B, and 7C show graphs illustrating laboratory pyrolysis, kinetics optimization and extrapolation to geological condition according to one or more embodiments. In some embodiments, the method and the system focus on bulk kinetics. In this regard, artificial maturation techniques to obtain bulk kinetic parameters may include open-system pyrolysis in the manner shown in FIG. 7A (e.g., Rock-Eval, SR Analyzer, HAWK, POPI-TOC, Pyromat) using multiple constant heating-rates. Because kerogen is heterogeneous, simplification in kinetic analysis and basin modeling comprises a discrete distribution of Ea values at one kcal/mol interval with a common A as shown in FIG. 7B.

In some embodiments, the procedure for determination of bulk kinetic parameters may include conducting pyrolysis on an immature source rock sample to generate reaction rate data in multiple heating rates experiments. For example, inverting kinetic parameters Ea and A may be fitted by calculating the parameters with measured reaction rates. As shown in FIG. 7A, graph 700 shows experimental and calculated pairs 701, 702, 703, 704, and 705. The experimental and calculated pairs may be distributed over discrete values along various temperature values.

In some embodiments, the procedure for determination of bulk kinetic parameters may include using a discrete distribution of Ea values at 1-kcal/mol interval with a common A to obtain kinetic parameters. As shown in FIG. 7B, graph 710 shows percentages (such as 711, 712, and 713) for values of activation energies that show a number of activation energy incidences over time.

In some embodiments, the procedure for determination of bulk kinetic parameters may include applying the kinetics in a geological heating rate (i.e., 1° C./Ma, where Ma are millions of years) to test the reasonableness of the parameters and estimate the onset of oil window and the critical point. As shown in FIG. 7C, graph 715 shows fraction reactions (such as 716 and 717) for values of temperatures that show transformation points over time. In some embodiments, the kinetic parameters may be directly imported into basin modeling software to quantify the process of hydrocarbon generation from kerogen transformation and create thermal maturity and transformation maps. In this regard, all derived kinetics may be applied with a geological heating-rate (based on thermal history) to test the respective reasonableness and reactivity before implementing measured kinetics in the basin model. The extrapolation may be conducted in kinetics software (e.g., Kinetics2015) or kinetics module of basin modeling software (e.g., PetroMod), providing a transformation ratio TR curve (as shown in FIG. 7C) to estimate an onset temperature and time of oil window (i.e., TR=10%) and a critical point (i.e., TR=50%) for a given petroleum system.

FIG. 8 shows a cross-plot of weighted average Ea and A on a logarithmic scale to evaluate thermal reactivity and maturity of source rock. A number on X and Y axes and the positions of dashed lines may be different in a case by case basis. The arc arrow indicates a direction of increasing maturity. This representation may be performed using a color gradient that matches the dashed arrows corresponding to wells 1, 2, and 3 at their respective intersection points. The arrows indicate a direction of decreasing reactivity. In this case, points A, B, and C represent samples in an immature source rock formation from well 1; points D, E, and F are samples from the same source rock formation within oil-window maturity from well 2; and points G, H, and I are samples from the same source rock formation within gas-window from well 3.

As described above, the kinetics data (WA-Ea and A) is grouped for a source rock formation from a well, and an exponential trend line for the data may be generated. With the assumption of similar maturity for a source rock formation in a well, the trend line on the WA-Ea and log A cross-plot presents a straight line, and the slope of the line is a function of averaged maturity for the source rock formation in the well. The average maturity may be marked based on $T_{max}$ from or other maturity measurement for the group of samples. The process may be repeated to create more trend lines on the cross-plot. For a very thick source rock formation in a well, the kinetics data may be divided into sub-groups based on depth and rock properties to ensure the variation of Ro (i.e., vitrinite reflectance) or VRE (i.e., Ro equivalent) to be small enough (e.g., less than 0.1%, in each sub-group). $T_{max}$ may be used to estimate VRE. Then trend lines may be made for each sub-group. For a dataset that cannot be grouped by wells (e.g., scattered kinetic parameters from publications), the data may be divided into maturity groups (e.g., <0.5%, 0.5~0.6%, 0.6~0.7%, . . . ), then trend lines may be made for each maturity group.

Finally, maturity lines may be determined on the cross-plot to show a clockwise increase of maturity, where there is a systematic shift in Ea distribution with increasing maturity.

As shown in FIGS. 5 and 6, evaluating maturity of source rock samples may account for the maturity gradient of FIG. 8. In this regard, the maturity of a new source rock sample may be qualitatively estimated based on their WA-Ea and A values. For example, the maturities in FIG. 8 may be related by (A≈B≈C)<(D≈E≈F)<(G≈H≈I). Further, as shown in FIGS. 5 and 6, evaluating and ranking reactivities of source rock samples may account for a change in reactivity in the samples. For example, the reactivities in FIG. 8 may be related when source rock samples have similar maturities (e.g., Ro variation <0.1%) or when a source rock formation in a well may be determined based on a reactivity trend line. For example, in FIG. 8, the reactivities may be related by A>B>C, D>E>F, and G>H>I.

Examples shown in FIGS. 9, 10A, and 10B demonstrate reactivities evaluated by the method and the system described herein. In some embodiments, curves perpendicular to the dashed lines may be drawn to rank the reactivities of source rocks. As shown on FIG. 8, two ranking curves may be arbitrarily drawn to identify three reactivity categories: high, medium, and low. Based on the trend line for immature source rocks (e.g., well 1), respective WA-Ea values for these reactivity categories may be less than 54 kcal/mol, between 54 a kcal/mol and 58 kcal/mol, and less than 58 kcal/mol. In this case, reactivities of source rocks with different maturities may be approximately assessed as (A≈D)>(B≈E≈G)>(C≈F≈I). The ranking curves may be refined by measuring kinetic parameters of a series of source rock samples that experience different extents of artificial maturation. More rankings may be done to build a source rock kinetics model with more details.

The ranking of reactivities may provide a solution to assign kinetic parameters derived from immature source rock sample for mature units of the source rock. In a source rock formation, the method and the system assume that no significant change in organofacies, the kinetics of immature source rock unit represent the best kinetics of those mature source rock units in the same ranking of reactivities. For example, source rock units C, F, and I shown in FIG. 8 may be in a same reactivity category (low). In this regard, C, rather than A or B, may be the best kinetics representative for F and I. Further, it may be better to use the kinetics derived from immature source rock unit C, rather than the kinetics average or the weighted-average of A, B, and C, in basin modeling for the area outlined by C, F, and I. The direct use of the average or weighted-average kinetics may lead to a loss of details in hydrocarbon generation caused by the different reactivities in a source rock.

In FIGS. 9, 10A, 10B, 11A, 11B, 11C, 11D, 12A, 12B, and 13, testing implementing the method and the system is shown referencing two different datasets. A first case evaluates measured kinetics of a source rock formation from different wells of different maturities. A second case evaluates published and measured kinetics derived from different source rock formations of the same maturity level (e.g., immature).

The first case shows measured kinetics from three wells. The source rock is a marine source rock formation (i.e., type II kerogen) from four wells in Saudi Arabia as shown in FIG. 9. The maturity is determined by $T_{max}$ and graptolite reflectance because of the lack of vitrinite particles. In this case, the wells T, S, M, and A correspond to an immature well, a very early-oil maturity, a late-oil maturity, and a dry-grass maturity, respectively. No kinetic parameters are determined from well A because there is no undefined S2 peak for kinetics analysis on samples from well A. In the test, the pyrolysis instrument is an open system (e.g., HAWK). Laboratory heating-rates for kinetics analysis are between 3° C./min and 30° C./min, inclusive. The mathematics model for kinetic parameters include a common A and a discrete distribution of Ea with 1 kcal/mol spacing as shown in FIGS. 10A and 10B. The geological heating rate for extrapolation (i.e., generating transformation curves) is 1° C./Ma.

In particular, FIG. 9 shows a table including sample information, source-rock pyrolysis data, and reprocess kinetic parameters by the invented method. In FIG. 9, the "Depth" refers to the depths of the source rock formation in Well T<Well S<Well M<Well A. The "Seq.#" refers to a number of depth sequence shown on FIGS. 11A, 11B, 11C, 11D, 12A, 12B, and 13. The "VRE.t" refers to Virtrine Reflectance Equivalent calculated by VRE=(0.01867*T max)–7.306. the "GRo" refers to Graptolite Reflectance. The "VRE.g" refers to Virtrine Reflectance Equivalent estimated based on Gro. The "A" refers to a common frequency factor for a discrete Ea distribution. The "WA-Ea" refers to a weighted average Ea of a discrete Ea distribution calculated using equation (2).

FIGS. 11A, 11B, 11C, and 11D, show examples of kinetic parameters showing a common A and a discrete Ea distribution in Case 1 across graphs 1110, 1120, 1130, and 1140. In these FIGS. 11A, 11B, 11C, and 11D, an open-system pyrolysis with two heating rates (3° C./min and 30° C./min) by HAWK are used to generate pyrolysis data for kinetics calculation conducted in Kinetics2015 software.

Figure 12A:
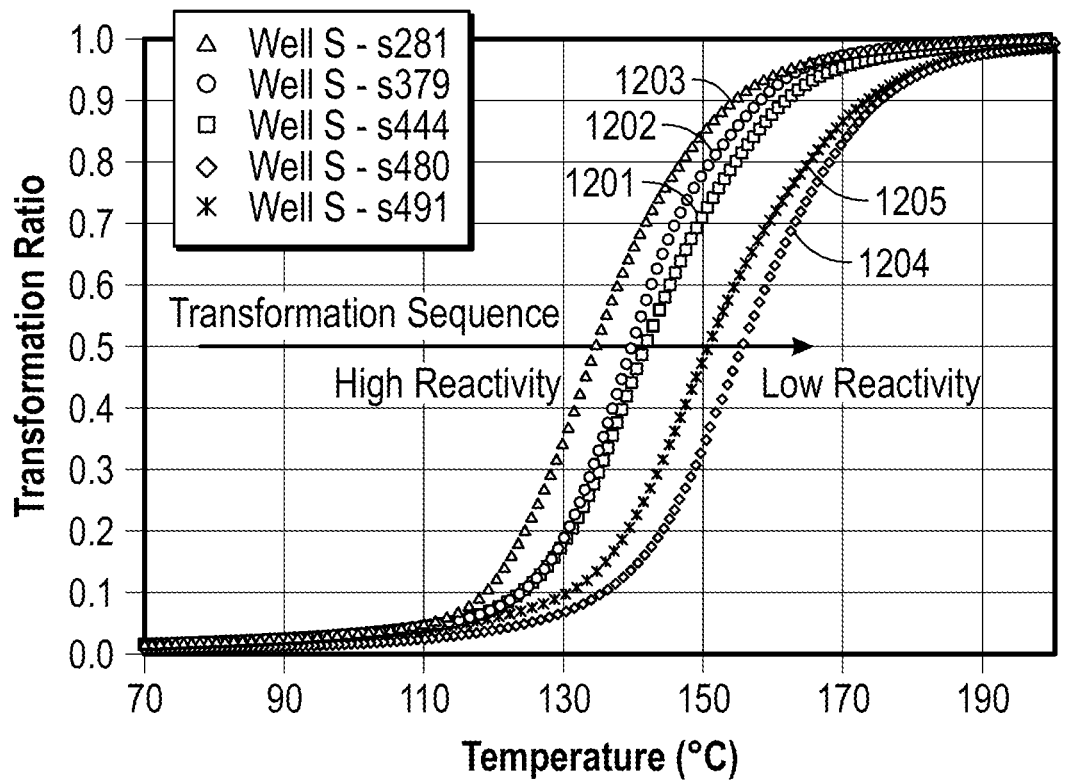
FIG. 12A shows a plot of transformation curves generated by applying kinetic parameters in an assumed thermal history in accordance with one or more embodiments.
Figure 12B:
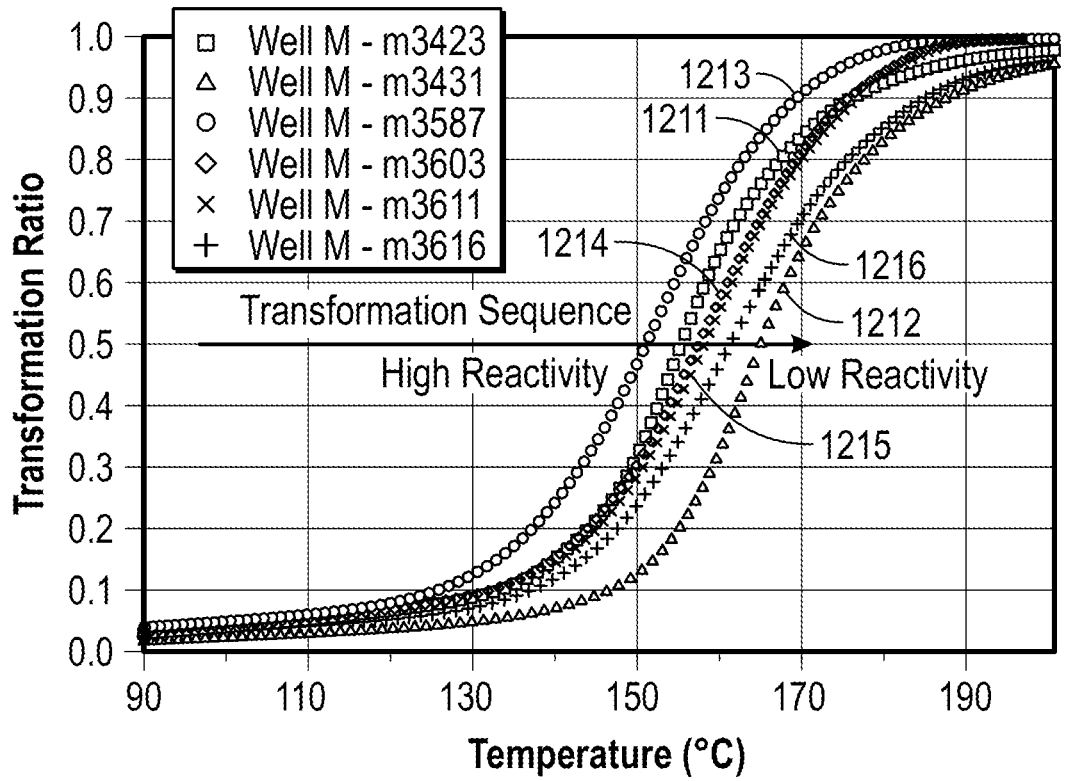
FIG. 12B shows a plot of transformation curves generated by applying kinetic parameters in an assumed thermal history in accordance with one or more embodiments.

FIGS. 12A and 12B show evaluation by transformation curves (1201, 1202, 1203, 1204, and 1205 or 1211, 1212, 1213, 1214, and 1215) generated using Kinetics2015 for the wells discussed with respect to FIGS. 9, 10A, and 10B. In this case, the thermal reactivities are curve 1201>curve 1202>curve 1203>curve 1205>curve 1204 for well S and curve 1213>curve 1211>curve 1215>curve 1214>curve 1216>curve 1212 for well M. FIGS. 12A and 12B show transformation ratio curves generated by applying the discrete kinetic model (i.e., a common A and Ea discrete distribution) with a geological heating rate 1° C./Ma in Kinetics2015 software. Further, the comparison of transformation curves (i.e., transformation sequence) is the current solution to evaluate reactivity. In this case, from left to right, the transformation of kerogen to hydrocarbon shows that higher temperature is needed by becoming more difficult and indicating the decrease of reactivity of source rock samples. The numbers on the curves show depth sequence, curve 1201 is the shallowest sample.

Figure 13:
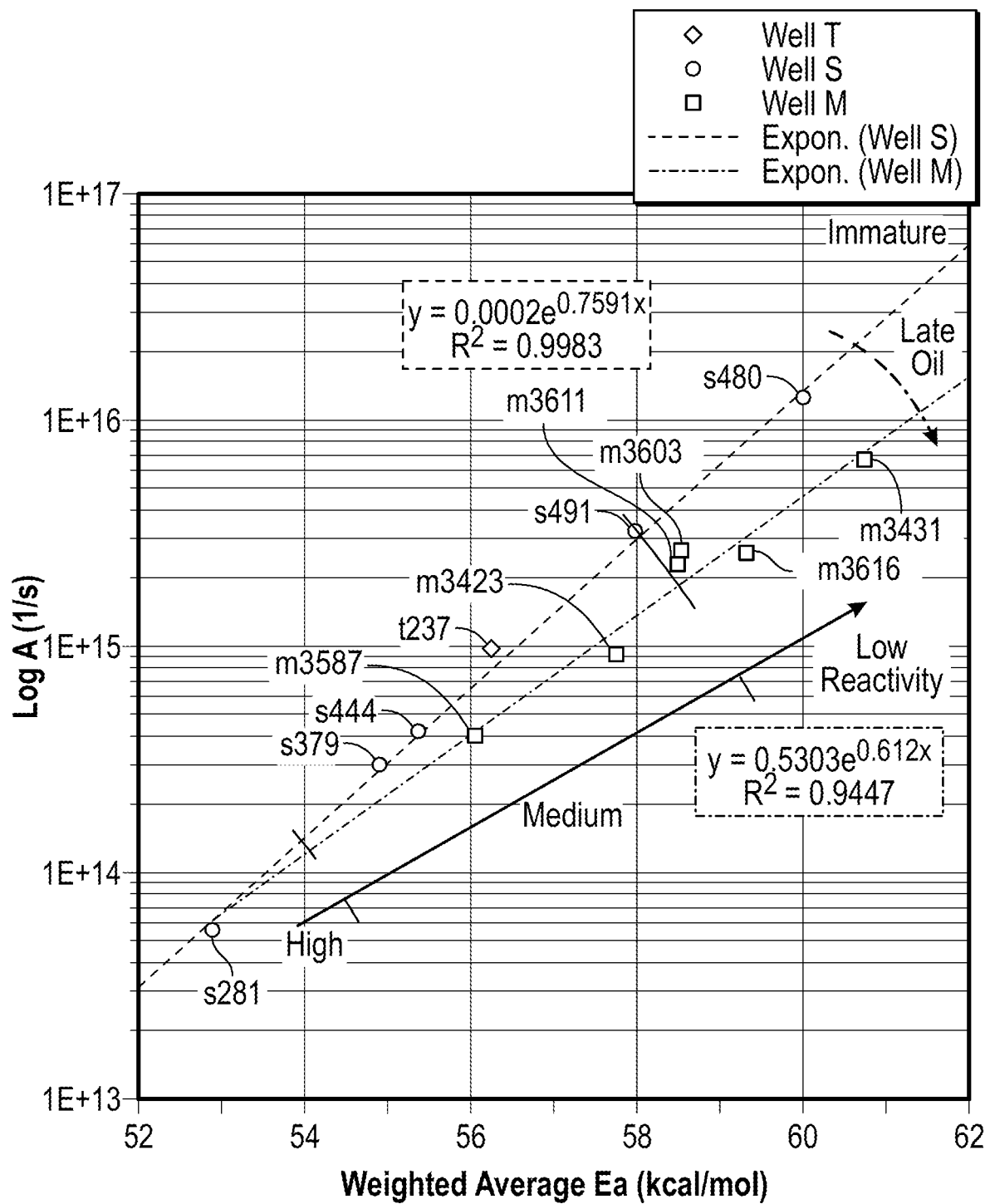
FIG. 13 shows a plot including kinetic parameters reprocessed by the method for evaluation of source rock reactivity in accordance with one or more embodiments.

FIG. 13 shows an evaluation using the method and the system described herein. In FIG. 13, the method and the system are used to evaluate thermal maturities and reactivities. Two exponential trend lines are drawn for data of Well S and Well M, respectively, showing lineal relationship between WA-Ea and Log (A). The thermal maturity includes two exponential trend lines are drawn for data of Well S and Well M, respectively, showing linear relationship between WA-Ea and Log (A). In this case, the maturities are related as Well T<Well S<Well M. The thermal activities are curve 1201>curve 1202>curve 1203>curve 1205>curve 1204 for well S and curve 1213>curve 1211>curve 1215>curve 1214>curve 1216>curve 1212 for well M. In FIG. 13, the ranking of thermal relativity follows: low relativity in well S; medium relativity in well T, well S curve 1202, curve 1203, and curve 1205 and well M curve 1201 and curve 1213; and high relativity in well S (4) and well M curve 1212, curve 1214, curve 1215, curve 1216.

In one or more embodiments, based on the results from FIGS. 9-13, the order of maturity evaluated by invention is constant with the assessment by T max and graptolite reflectance. The slope of the trend line might be a proxy for maturity. The thermal reactivity evaluated by the invention is constant when assessed by transformation curves generated in Kinetics2015 software. The method and the system provide ranking of reactivity of source rocks with different maturities.

Figure 14:
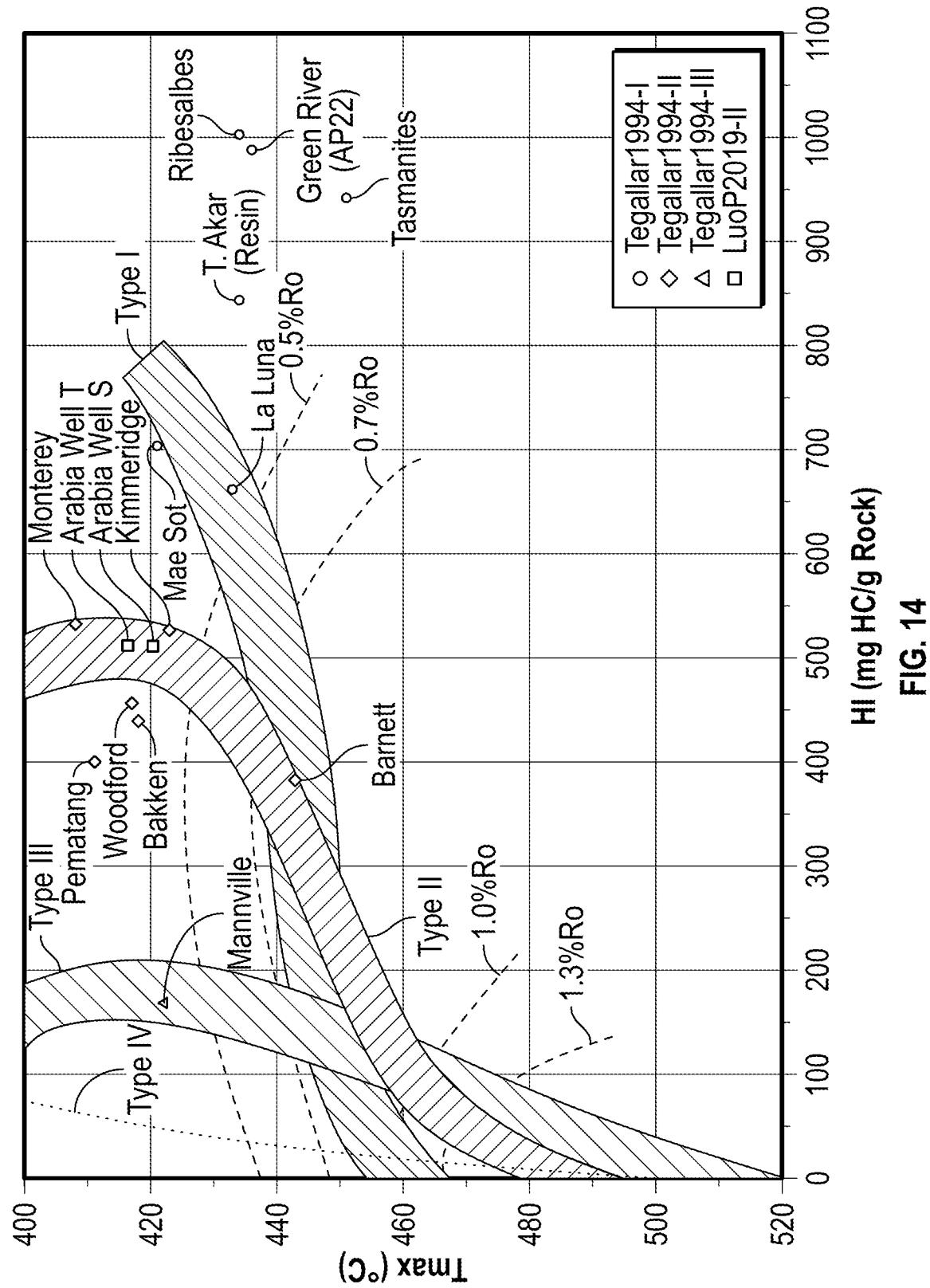
FIGS. 14 and 15 show graphs for kerogen types and transformation curves of source rocks that are tested with the method in accordance with one or more embodiments.
Figure 15:
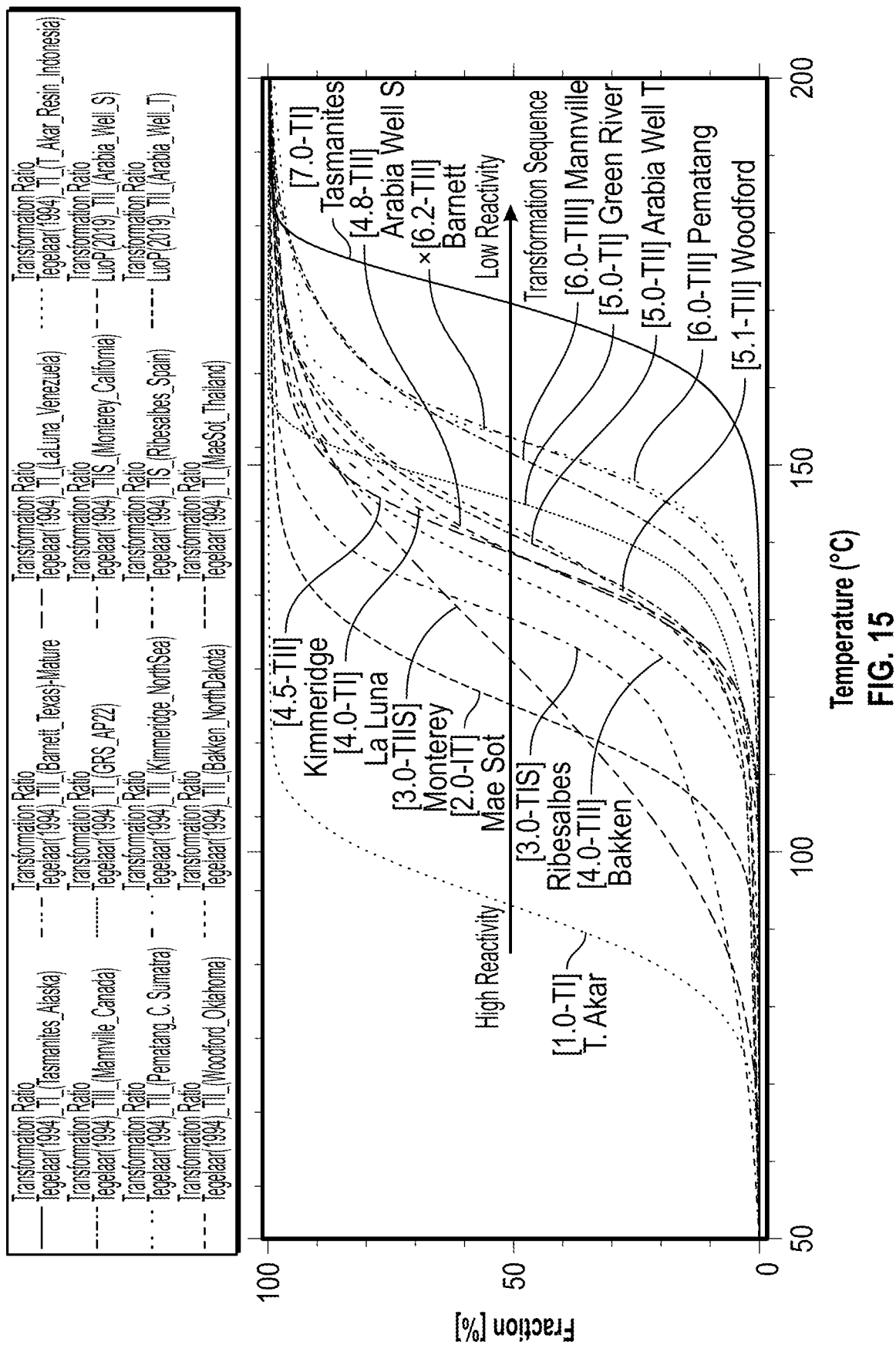
Figure 16:
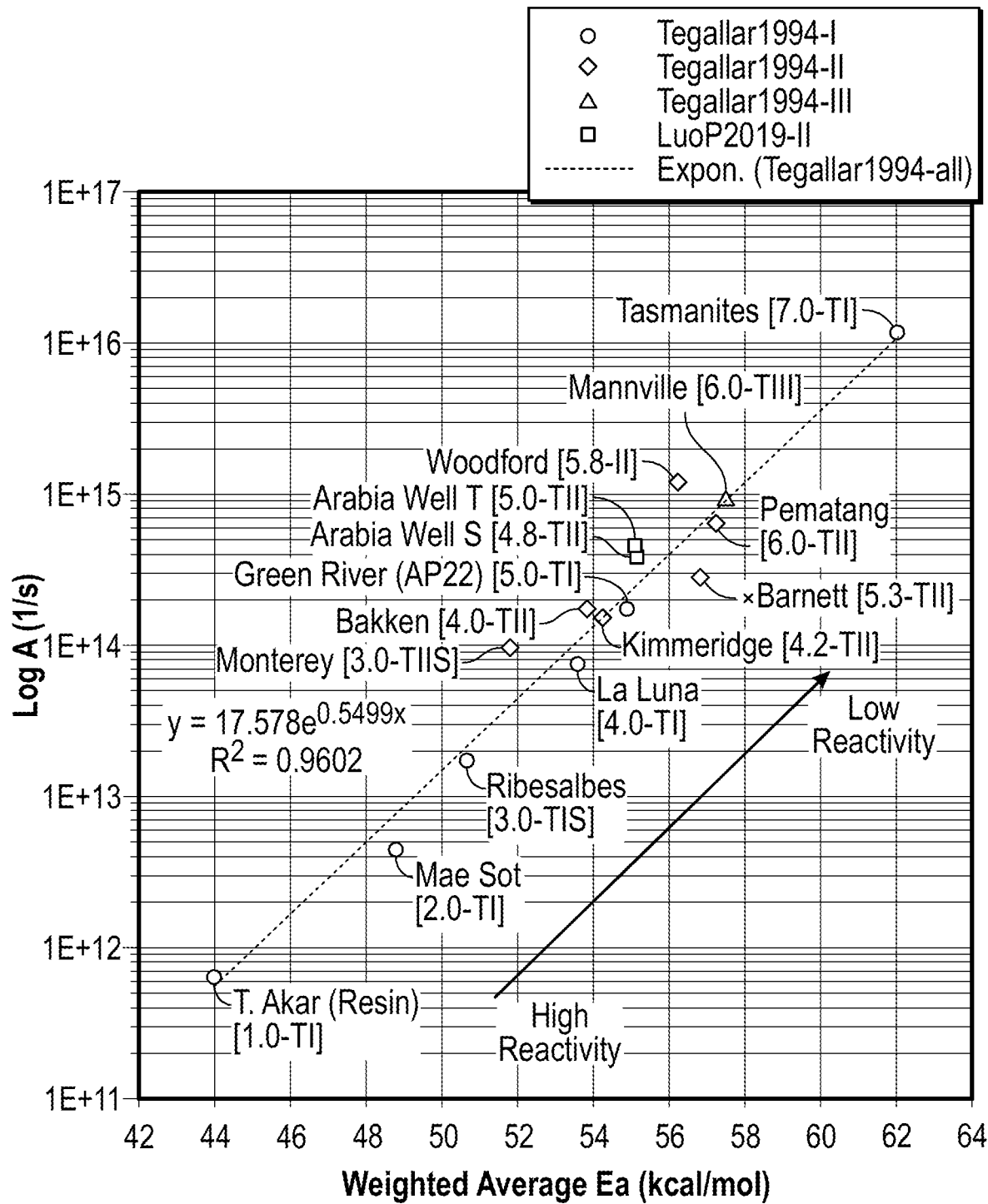
FIG. 16 shows a plot including kinetic parameters reprocessed by the method for source rocks that are tested with the method in accordance with one or more embodiments.

FIGS. 14, 15, and 16, testing implementing the method and the system is shown referencing two different datasets. In this case, measured kinetics are compared to published kinetics. The source rock sample measured is a marine source rock formation (i.e., type II kerogen) in Saudi Arabia. Two samples from Well T and Well S are used in this case. The published kinetics are all source rocks with reported kinetic parameters published by Tegelaar and Noble (1994). The kerogen types are determined as Type I (TI)/Type I-sulfur (TIS), Type II (TII)/Type II-sulfur (TII-S) and Type III (TIII) based on FIG. 14 and other geochemical parameters (Tegelaar and Noble, 1994). Their kinetic parameters are available in Kinetics Editor of PetroMod. The maturity shows that all samples except Barnett shale are immature based on Rock-Eval HI and $T_{max}$ data as shown in FIG. 14. The estimated Ro of the Barnett shale based on FIG. 14 is more than 0.70%, and the VRE suggested by the empirical equation of VRE and $T_{max}$ (Hackley and Cardott, 2016) is 0.96%; although Tegelaar and Noble (1994) reported the relatively low Ro value (0.53%). Pyrolysis instruments are similar to an open system measured in HAWK as published by Pyromat II. Laboratory heating-rates for kinetic analysis are measured as 1° C./min, 3° C./min, 10° C./min, 30° C./min, and 50° C./min. Kinetic parameters are published as 1° C./min, 5° C./min, 15° C./min, and 50° C./min. The mathematics model for kinetic parameters are a common A and a discrete distribution of Ea with 1 kcal/mol spacing. The geological heating-rate for extrapolation (i.e., generating transformation curves) is 1° C./Ma.

In one or more embodiments, FIG. 14 shows evaluation by transformation curves generated in PetroMod software. In this case, the thermal reactivities are catalogued as follows: Type I and III: T. Akar (TI)>Mae Sot (TIS)>Ribesalbes (TI)>La Luna (TI)>Green River (TI)>Mannville (TIII)>Tasmanites (TI); and Type II: Monterey (TIIS)>Bakken (TII)>Kimmeridge (TII)>Arabia Well S (TII)>Arabia Well T (TII)>Woodford (TII)>Pematang (TII)>Barnett (TII). In this case, the Barnett shale used in the analysis is probably a mature sample, so its kinetics and reactivity are not comparable to other source rocks (i.e., immature samples). The transformation curve of an immature Barnett shale should be left shift because of the maturity effect on Ea distribution, and its reactivity would be in the middle of the sequence for Type II kerogens.

In one or more embodiments, the ranking of thermal reactivity may be an arbitrary number for ranking of reactivities can made based on the sequence of transformation. In this case, [1.0] is the most reactive source rock, and [7.0] is the most stable source rock in the case. For type I and III: [1.0] T. Akar>[2.0] Mae Sot>[3.0] Ribesalbes>[4.0] La Luna>[5.0] Green River>[6.0] Mannville>[7.0] Tasmanites. In the reactivity ranking of type I and III, rankings are estimated for type II: [3.0] Monterey>[4.0] Bakken>[4.5] Kimmeridge>[4.8] Arabia Well S>[5.0] Arabia Well T>[5.1] Woodford>[6.0-TII] Pematang>[6.2-TII] Barnett.

In one or more embodiments, FIG. 15 shows an evaluation showing a thermal maturity that includes exponential trend lines drawn for all published data, showing a explicit lineal relationship between WA-Ea and Log (A), which generally agrees the maturity assessment. In FIG. 15, thermal reactivities of Type I and III are: T. Akar (TI)>Mae Sot (TI)>Ribesalbes (TIS)>La Luna (TI)>Green River (TI)>Mannville (TIII)>Tasmanites (TI); and Type II: Monterey (TIIS)>Bakken (TII)>Kimmeridge (TII)>Arabia Well S (TII)≈Arabia Well T (TII)>Barnett (TII)>Woodford (TII)>Pematang (TII). The kinetic parameter and relativity of the Barnett shale is not comparable because of its maturity.

In FIG. 15, ranking of thermal reactivities including an arbitrary number for ranking of reactivities. In this case, [1.0] is the most reactive source rock, and [7.0] is the most stable source rock in the case. For type I and III: [1.0] T. Akar>[2.0] Mae Sot>[3.0] Ribesalbes>[4.0] La Luna>[5.0] Green River>[6.0] Mannville>[7.0] Tasmanites. In the reactivity ranking of type I and III, rankings are estimated for type II: [3.0] Monterey>[4.0] Bakken>[4.2] Kimmeridge>[4.8] Arabia Well S>[5.0] Arabia Well T>[5.3-TII] Barnett>[5.8] Woodford>[6.0-TII] Pematang. The kinetic parameter and relativity of the Barnett shale is not comparable because of its maturity.

In this case, FIGS. 14 and 15 provide very similar ranking of reactivities for source rocks at a same maturity level (in the case "immature") compared to the evaluation by transformation sequence. In some embodiments, the method and the system use WA-Ea to replace Ea distribution in geological extrapolation, which would only quantify the averaged kinetic behavior and the reactivity of the source rock in the main hydrocarbon generation window. The simplification facilitates the use of kinetic parameters in reactivity evaluation but may loss details at the beginning and/or late stage of kerogen conversion (as shown on FIG. 14, when TR<10% and >90%).

FIG. 14 shows a Rock-Eval HI vs. T max cross-plot demonstrating kerogen types and their maturation trends, modified from Cornford et al., (1998). Two samples of a marine source rock (Type II) from Saudi Arabia are measured and 13 source rocks (Type I: green, Type-II: light blue, Type III: purple) from Tegelaar and Noble (1994) as the examples of published data are used in the testing described in FIGS. 14 and 15. All samples except Barnett shale are immature. The estimated Ro of the Barnett shale based on the plot should be more than 0.70%, although the author reported the relatively low Ro value (0.53%). The bulk kinetic parameters of the 13 source rocks are available in PetroMod.

FIG. 15 shows transformation ratio curves generated by applying the discrete kinetic model (a common A and Ea discrete distribution) with a geological heating rate (1° C./Ma) in PetroMod software. FIG. 15 shows that comparison of transformation curves (i.e., transformation sequence) is the current solution to evaluate reactivity. In this case, from left to right, the transformation of kerogen to hydrocarbon needs higher temperature and becomes more difficult, indicating the decrease of reactivity of source rock. For both type-I (solid curves) and type-III source rocks, reactivities: T. Akar (TI)>Mae Sot (TI)>Ribesalbes (TIS)>La Luna (TI)>Green River (TI)>Mannville (TIII)>Tasmanites (TI); for all type-II source rocks (dashed curves), Monterey (TIIS)>Bakken (TII)>Kimmeridge (TII)>Arabia Well S (TII)>Arabia Well T (TII)>Woodford (TII)>Pematang (TII)>Barnett (TII). Further, the Barnett shale used in the analysis is probably a mature sample. The numbers close to the curves are the arbitrary rankings of reactivities based on the sequence of transformation, respectively for Type I & III and Type II. In this case, [1.0] is the most reactive source rock, and [7.0] is the most stable source rock in the case.

FIG. 16 shows an example in which the method and the system are used to evaluate thermal maturities and reactivities. An exponential trend line shows a very good lineal relationship between WA-Ea and Log (A), which generally agrees the maturity assessment (i.e., constantly immature except Barnett) based on FIG. 13. For both Type I (circles) and type-III (triangles) source rocks, reactivities: T. Akar (TI)>Mae Sot (TI)>Ribesalbes (TIS)>La Luna (TI)>Green River (TI)>Mannville (TIII)>Tasmanites (TI); and for all type-II (diamonds) source rocks, Monterey (TIIS)>Bakken (TII)>Kimmeridge (TII)>Arabia Well S (TII)≈Arabia Well T (TII)>Barnett (TII)>Woodford (TII)>Pematang (TII).

Figure 17:
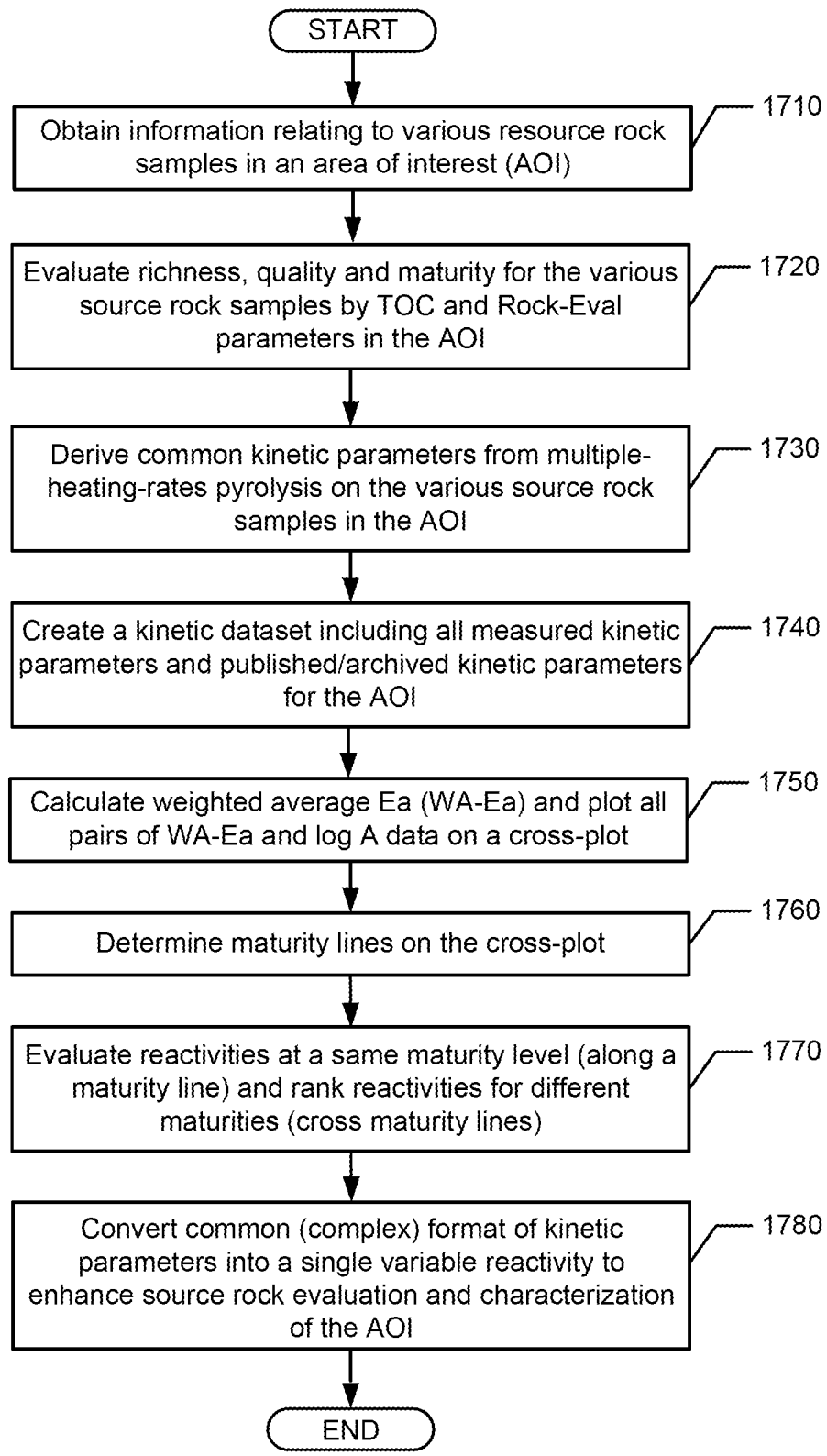
FIG. 17 shows a flowchart in accordance with one or more embodiments.

FIG. 17 shows a flowchart in accordance with one or more embodiments. Specifically, FIG. 17 describes a method for evaluating reactivity in source rock evaluation. In some embodiments, the method may be implemented using the control system 360 of the collection system 300 described in reference to FIG. 3. Further, one or more blocks in FIG. 17 may be performed by one or more components as described in FIGS. 1-3. While the various blocks in FIG. 17 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 1710, information relating to various resource rock samples is obtained from an area of interest (AOI). The information may be obtained using the collecting tool 160 as described in FIGS. 1-3. The source rock samples may be collected and tested in a same location using an in situ laboratory equipment room, which may be similar to the laboratory equipment room discussed in reference to FIG. 3. The samples may be additionally, or alternatively, tested in a location that is at a remote distant from the location where the source rock samples were collected.

In Block 1720, organic matter richness, quality, and maturity for the various source rock samples are evaluated by TOC and Rock-Eval from the AOI. In laboratory testing procedures, richness, quality, and maturity may be tested and evaluated using the source rock samples collected of the information thereof. As described above, the thermal maturities may be determined using open-system pyrolysis 510 while evaluating organic matter in a source rock.

In Block 1730, common kinetic parameters are derived from multiple-heating-rates pyrolysis on the various source rock samples in the AOI. Under the common kinetic model, a discrete distribution of Ea values may be paired with a common A, to obtain kinetic parameters.

In Block 1740, a kinetic dataset is created including all measured kinetic parameters, published kinetic parameters, and archived kinetic parameters. The various kinetic parameters corresponding to the AOI. As noted in FIGS. 4-13, the various kinetic parameters are collected, compiled, and compared to determine changes in the process of evaluating kinetic parameters from the information obtained. As described in reference to FIG. 5, the open-system pyrolysis 510 may be followed by heat-rates experiments 530 to generate the pyrolysis data for deriving the kinetic parameters 540 that used for the characterization of kinetic parameters 550 and the kinetic evaluation 570. The pyrolysis data may be processed in kinetics analysis software (e.g., Kinetics2000, Kinetics05, Kinetics2015) or manual regression and parameter fitting to derive the kinetic parameters 540.

In Block 1750, the weighted average Ea is calculated using Equation (2) and all pairs of WA-Ea and log A are plotted on a cross-plot. The kinetic parameters 540/624a-624c are weighted and averaged to generate a cross-plot in the manner discussed with respect to FIGS. 8-10. As noted above, the cross-plot of weighted average of the kinetic parameters 552 or 626a-626c may be plotted on a logarithmic scale to evaluate thermal reactivity and maturity of the source rock. In FIG. 8, because the arc arrow indicates the direction of increasing maturity, the maturity of a new source rock sample may be qualitatively estimated based on its derived kinetic parameters 552 or 626a-626c.

In Block 1760, maturity lines are determined in the cross-plot. The kinetic data (WA-Ea and A) is grouped by wells or maturity ranges. For the data from a well or a certain maturity range, an exponential trend line (maturity line) representing the variation of source rock kinetics at the same maturity level may be generated in the cross-plot. As there is a systematic shift in Ea distribution with increasing maturity, the trend lines may show a clockwise increase of maturity. In this case, multiple source rock samples are graphed to visually identify the maturities of these samples with respect to one another.

In Block 1770, reactivities are evaluated at a same maturity level and reactivities are ranked for different maturities. As shown in FIG. 8, the arrow of maturity line indicates the decreasing of reactivity at a same maturity level and reactivities may be ranked crossing maturity lines for source rocks at different maturities. Generating the graphical representation of the data of source rock kinetics provides a quick assessment of reactivity without complex calculation and basin modeling.

In Block 1780, complex format of kinetic parameters is converted into a single variable of reactivity for source rock. The variable is easier to use than common kinetic parameters in source rock evaluation and characterization of the area of interest.

Figure 18:
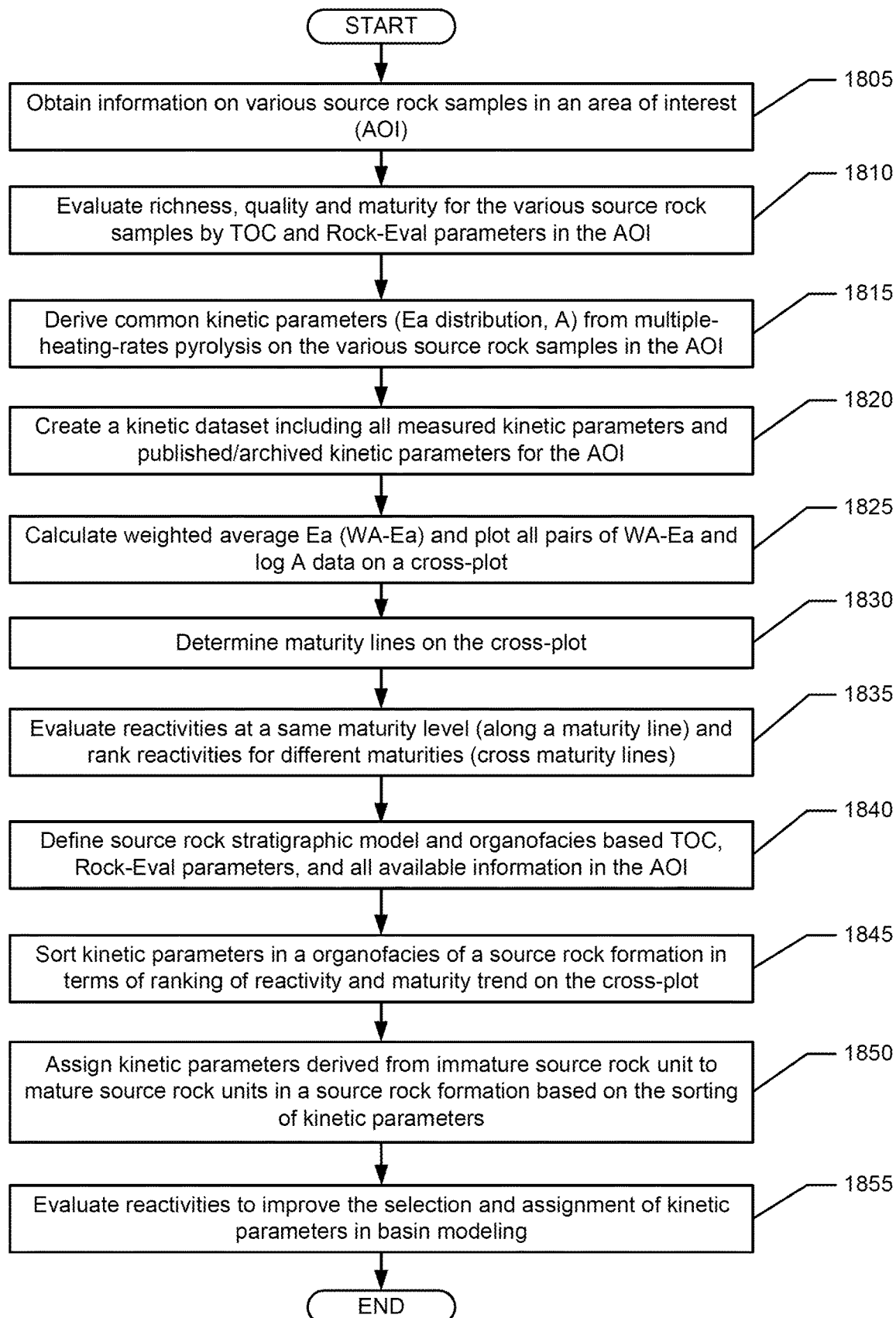
FIG. 18 shows a flowchart in accordance with one or more embodiments.

FIG. 18 shows a flowchart in accordance with one or more embodiments. Specifically, FIG. 18 describes a method for evaluating reactivity in source rock evaluation to improve the selection and assignment of kinetic parameters in basin modeling. In some embodiments, the method may be implemented using the control system 360 of the collection system 300 described in reference to FIG. 3. Further, one or more blocks in FIG. 18 may be performed by one or more components as described in FIGS. 1-3. While the various blocks in FIG. 18 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 1805, information relating to various resource rock samples is obtained for an AOI. As described in reference to Block 1710, the source rock samples may be collected and tested in a same location using an in situ laboratory equipment room, which may be similar to the laboratory equipment room discussed in reference to FIG. 3. The samples may be additionally, or alternatively, tested in a location that is at a remote distant from the location where the source rock samples were collected.

In Block 1810, as described in reference to Block 1720, organic matter richness, quality, and maturity for the various source rock samples are evaluated by TOC and Rock-Eval from the AOI. As described above, the parameters may be determined using open-system pyrolysis 510 while evaluating organic matter in a source rock.

In Block 1815, as described in reference to Block, common kinetic parameters are derived from multiple-heating-rates pyrolysis on the various source rock samples in the AOI. Under the common kinetic model, a discrete distribution of Ea values may be paired with a common A, to obtain kinetic parameters.

In Block 1820, a kinetic dataset is created including all measured kinetic parameters, published kinetic parameters, and archived kinetic parameters. In particular, as described in reference to Block 1740 and as described in reference to FIG. 5, the open-system pyrolysis 510 may be followed by heat-rates experiments 530 to generate the pyrolysis data for deriving the kinetic parameters 540 that used for the characterization of kinetic parameters 550 and the kinetic evaluation 570. The pyrolysis data may be processed in kinetics analysis software (e.g., Kinetics2000, Kinetics05, Kinetics2015) or manual regression and parameter fitting to derive the kinetic parameters 540.

In Block 1825, as described in reference to Block 1750, the weighted average Ea is calculated using Equation (2) and all pairs of WA-Ea and log A are plotted on a cross-plot. The kinetic parameters 540 or 624a-624c are weighted and averaged to generate a cross-plot in the manner discussed with respect to FIGS. 8-10. As noted above, the cross-plot of weighted average of the kinetic parameters 552 or 626a-626c may be plotted on a logarithmic scale to evaluate thermal reactivity and maturity of the source rock. In FIG. 8, because the arc arrow indicates the direction of increasing maturity, the maturity of a new source rock sample may be qualitatively estimated based on its derived kinetic parameters 552 or 626a-626c.

In Block 1830, as described in reference to Block 1760, maturity lines are determined in the cross-plot. The kinetic data (WA-Ea and A) is grouped by wells or maturity ranges. For the data from a well or a certain maturity range, an exponential trend line (maturity line) representing the variation of source rock kinetics at the same maturity level may be generated in the cross-plot. As there is a systematic shift in Ea distribution with increasing maturity, the trend lines may show a clockwise increase of maturity. In this case, multiple source rock samples are graphed to visually identify the maturities of these samples with respect to one another.

In Block 1835, as described in reference to Block 1770, reactivities are evaluated at a same maturity level and reactivities are ranked for different maturities. As shown in FIG. 8, the arrow of maturity line indicates the decreasing of reactivity at a same maturity level and reactivities may be ranked crossing maturity lines for source rocks at different maturities. Generating the graphical representation of the data of source rock kinetics provides a quick assessment of reactivity without complex calculation and basin modeling.

Further, in Block 1835, thermal reactivities of a source rock are ranked at different thermal maturities. Ranking curves may be refined by measuring the kinetic parameters 540 or 622 of a series of source rock samples that experience different extents of artificial maturation. As noted above, more rankings may be done to build a source rock kinetics model with more details. The reactivities or rankings of reactivity may provide a new variable or dimension that is beyond parameters routinely measured for source rock evaluation (i.e., such as quantity, quality, and thermal maturity). For example, a source rock sample with higher reactivity may start generating hydrocarbons and reach peak generation before the source rock with lower reactivity.

In Block 1840, a source rock stratigraphic model and organofacies based TOC, Rock-Eval parameters, and all information available in the AOI are defined. The defined stratigraphic model and organofacies is used to represent the geological heterogeneity and organic geochemical characteristics of source rock, supporting to assign multiple kinetics in different units of a source rock formation.

In Block 1845, kinetic parameters are sorted in organofacies of a source rock formation in terms of the ranking of reactivities and maturity trend of the cross-plot. Kinetic parameters of different units in each organofaices of a source rock formation are processed as described in the reference to Block 1825-1835 and FIG. 13 to evaluate their reactivities. The kinetic parameters of source rock units with different maturities therefore can be sorted based on their organofacies and rank of reactivities.

In Block 1850, kinetic parameters derived from immature source rock unit are assigned to mature source rock units in a source rock formation based on the sorting of kinetic parameters. The thermal mature source rock unit may share the kinetic parameters derived from immature source rock unit in an organofacies if the two units are in the same rank of reactivities. In the state of the art in basin modeling, kinetic parameters derived from an immature source rock sample are used as a kinetic representative for a whole source rock formation in a basin, which is then used to simulate hydrocarbon generation and expulsion in the petroleum system derived from this source rock. As described above in reference to FIGS. 9, 11 and 12, because considerable regional and vertical variations exist in kinetics of a single source rock, even at a same well locality, using a single set of kinetic parameters and direct assigning kinetic parameters derived from immature source rock samples for those mature units of the source rock can not account for the changes of organofacies and kinetics in the entire formation. In this regard, the ranking of reactivities allows assigning kinetic parameters derived from immature source rock sample for those mature units of the source rock. In an organofacies of a source rock formation, the kinetics of immature source rock unit represent the best kinetics of those mature source rock units in the same ranking of reactivities.

In Block 1855, reactivities are evaluated to improve the selection and assignment of kinetic parameters in basin modeling. As discussed above, the invention describes a well-grounded approach to select kinetic parameters derived from immature source rock samples for mature source rock units and allow to assign multiple kinetic parameters for different units of a source rock formation in a sedimentary basin. Multiple kinetic parameters are incorporated into the source rock model to address the heterogeneity of organic matter and the vertical and lateral changes of kinetics in the source rock. In this regard, hydrocarbon generation and expulsion in the petroleum system will be improved by using better kinetic representative and multiple kinetic parameters, leading an optimized basin modeling.

Embodiments of the invention may be implemented using virtually any type of computing system, regardless of the platform being used. In some embodiments, the control system 350 may be computer systems located at a remote location such that data collected is processed away from the surface 370. In some embodiments, the computing system may be implemented on remote or handheld devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments of the invention.

Figure 19:
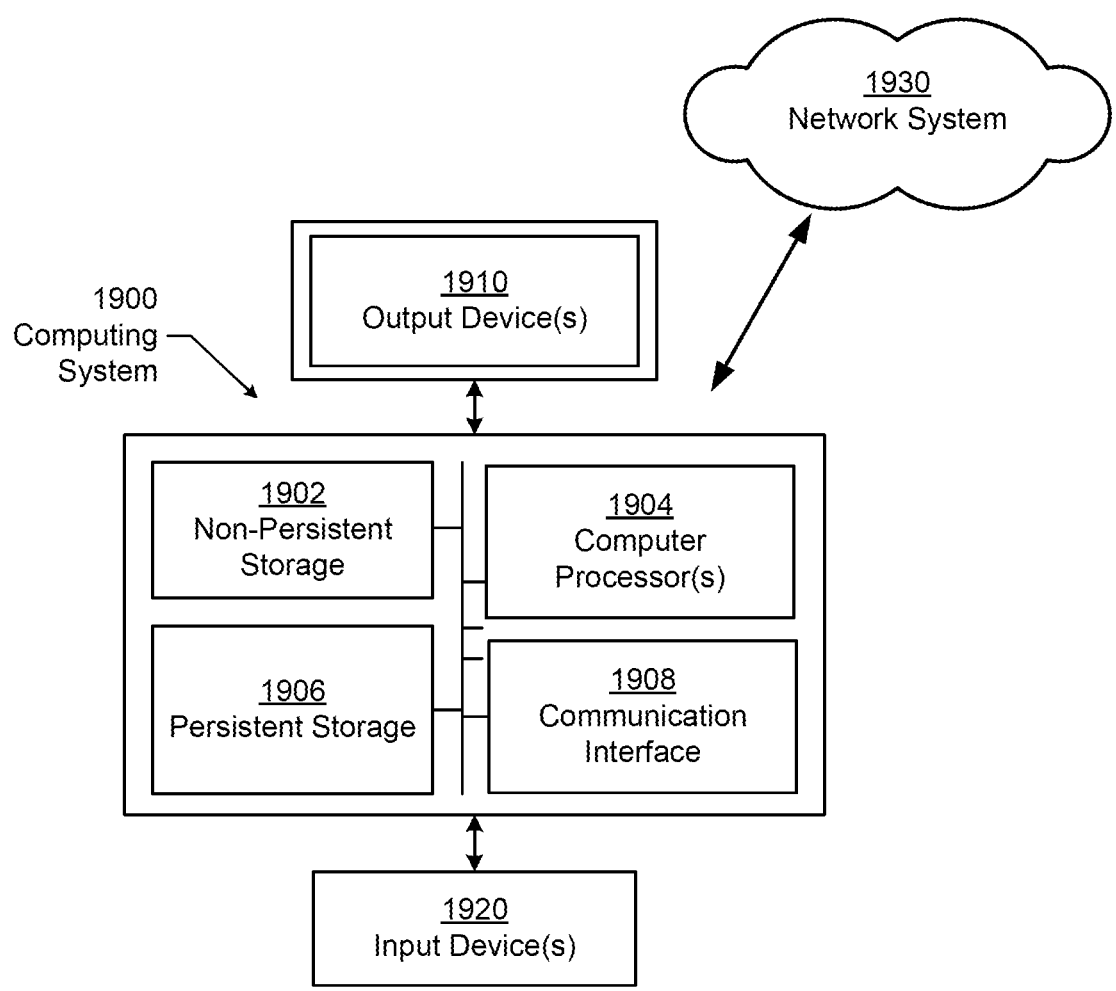
FIG. 19 shows a schematic diagram of a system in accordance with one or more embodiments.

As shown in FIG. 19, the computing system 1900 may include one or more computer processor(s) 1904, non-persistent storage 1902 (e.g., random access memory (RAM), cache memory, or flash memory), one or more persistent storage 1906 (e.g., a hard disk), a communication interface 1908 (transmitters and/or receivers) and numerous other elements and functionalities. The computer processor(s) 1904 may be an integrated circuit for processing instructions. The computing system 1900 may also include one or more input device(s) 1920, such as a touchscreen, keyboard, mouse, microphone, touchpad, electronic pen, or any other type of input device. In some embodiments, the one or more input device(s) 1920 may be the surface panel described in reference to FIGS. 1 and 3. Further, the computing system 1900 may include one or more output device(s) 1910, such as a screen (e.g., a liquid crystal display (LCD), a plasma display, or touchscreen), a printer, external storage, or any other output device. One or more of the output device(s) may be the same or different from the input device(s). The computing system 1900 may be connected to a network system 1930 (e.g., a local area network (LAN), a wide area network (WAN) such as the Internet, mobile network, or any other type of network) via a network interface connection (not shown).

In one or more embodiments, for example, the input device 1920 may be coupled to a receiver and a transmitter used for exchanging communication with one or more peripherals connected to the network system 1930. The receiver may receive information relating to one or more resource rock samples. The transmitter may relay information received by the receiver to other elements in the computing system 1900. Further, the computer processor(s) 1904 may be configured for performing or aiding in implementing the processes described in reference to FIGS. 18 and/or 19.

Further, one or more elements of the aforementioned computing system 1900 may be located at a remote location and be connected to the other elements over the network system 1930. The network system 1930 may be a cloud-based interface performing processing at a remote location from the well site and connected to the other elements over a network. In this case, the computing system 1900 may be connected through a remote connection established using a 5G connection, such as protocols established in Release 15 and subsequent releases of the 3GPP/New Radio (NR) standards.

The computing system in FIG. 19 may implement and/or be connected to a data repository. For example, one type of data repository is a database. A database is a collection of information configured for ease of data retrieval, modification, re-organization, and deletion. In some embodiments, the database includes published/measured data relating to the method and the system as described in reference to FIGS. 1-18.

While FIGS. 1-19 show various configurations of components, other configurations may be used without departing from the scope of the disclosure. For example, various components in FIG. 1-3 may be combined to create a single component. As another example, the functionality performed by a single component may be performed by two or more components.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed is:

1. A method for evaluating reactivity in source rock evaluation, the method comprising:
collecting, with a collecting tool, a plurality of source rock samples, the collecting tool comprising:
a sampling system configured to collect and store the plurality of source rock samples;
a sensing system configured to collect physical data from source rock samples;
a processing system configured to perform computational processes and store the physical data related to the source rock samples; and
a communication system configured to receive and transmit signals associated with the physical data related to the source rock samples;
obtaining, with a receiver, information relating to the plurality of source rock samples;
determining, with a processor coupled to the receiver, thermal reactivities of the plurality of source rock samples, the plurality of source rock samples being at a same level of thermal maturity in an area of interest,
interpreting, with the processor, kinetic parameters derived from the plurality of source rock samples; and
converting, with the processor, complex format of the kinetic parameters into a single variable for the reactivity for the source rock evaluation and characterization of the area of interest.

2. The method of claim 1, the method further comprising:
comparing, with the processor, published kinetic parameters, archived kinetic parameters, and measured kinetic parameters of the area of interest.

3. The method of claim 1, the method further comprising:
estimating, with the processor, the thermal maturity of each of the plurality of source rock samples based on the kinetic parameters interpreted.

4. The method of claim 1, wherein the thermal reactivity is chemical reactivity under thermal stress.

5. The method of claim 1, wherein the kinetic parameters interpreted are the kinetic parameters derived from thermally mature source rock samples.

6. The method of claim 1, wherein the kinetic parameters include a frequency factor A and a weighted average of $E_a$ distribution.

7. The method of claim 6, wherein the frequency factor A and the weighted average of the $E_a$ distribution are related to a gas constant R and a reaction temperature T.

8. The method of claim 7, wherein the frequency factor A, the weighted average of the $E_a$ distribution, the gas constant R, and the reaction temperature T are inputs of a basin modeling equation $k=Ae^{31-E_a/RT}$.

9. A system for evaluating reactivity in source rock evaluation, the system comprising:
a collecting tool configured to collect a plurality of source rock samples, the collecting tool comprising:
a sampling system configured to collect and store the plurality of source rock samples;
a sensing system configured to collect physical data from source rock samples;
a processing system configured to perform computational processes and store the physical data related to the source rock samples; and
a communication system configured to receive and transmit signals associated with the physical data related to the source rock samples;
a receiver that receives information relating to the plurality of source rock samples;
a processor that:
determines thermal reactivities of the plurality of source rock samples, the plurality of source rock samples being at a same level of thermal maturity in an area of interest,
interprets kinetic parameters derived from the plurality of source rock samples; and
converts complex format of the kinetic parameters into a single variable for reactivity source rock evaluation and characterization of the area of interest.

10. The system of claim 9, wherein the processor compares published kinetic parameters, archived kinetic parameters, and measured kinetic parameters of the area of interest.

11. The system of claim 9, wherein the processor estimates the thermal maturity of each of the plurality of source rock samples based on the kinetic parameters interpreted.

12. The system of claim 9, wherein the thermal reactivity is chemical reactivity under thermal stress.

13. The system of claim 9, wherein the kinetic parameters interpreted are the kinetic parameters derived from thermally mature source rock samples.

14. The system of claim 9, wherein the kinetic parameters include a frequency factor A and an weighted average of $E_a$ distribution.

15. The system of claim 14, wherein the frequency factor A and the weighted average of the $E_a$ distribution are related to a gas constant R and a reaction temperature T.

16. The system of claim 15, wherein the frequency factor A, the weighted average of the $E_a$ distribution, the gas constant R, and the reaction temperature T are inputs of a basin modeling equation $k=Ae^{31-E_a/RT}$.

17. A non-transitory computer readable medium storing instructions executable by a computer processor, the instructions comprising functionality for:
collecting, with a collecting tool, a plurality of source rock samples, the collecting tool comprising:
a sampling system configured to collect and store the plurality of source rock samples;
a sensing system configured to collect physical data from source rock samples;
a processing system configured to perform computational processes and store the physical data related to the source rock samples; and
a communication system configured to receive and transmit signals associated with the physical data related to the source rock samples;
obtaining information relating to the plurality of source rock samples;
determining thermal reactivities of the plurality of source rock samples, the plurality of source rock samples being at a same level of thermal maturity in an area of interest;
interpreting kinetic parameters derived from the plurality of source rock samples; and
converting complex format of the kinetic parameters into a single variable for reactivity source rock evaluation and characterization of the area of interest.

18. The non-transitory computer readable medium of claim 17, the instructions further comprising functionality for:

comparing published kinetic parameters, archived kinetic parameters, and measured kinetic parameters of the area of interest.

19. The non-transitory computer readable medium of claim 17, the instructions further comprising functionality for:

estimating the thermal maturity of each of the plurality of source rock samples based on the kinetic parameters interpreted.

20. The non-transitory computer readable medium of claim 17, wherein the kinetic parameters interpreted are the kinetic parameters derived from thermally mature source rock samples.

\* \* \* \* \*